(12) United States Patent
Huck et al.

(10) Patent No.: US 8,946,247 B2
(45) Date of Patent: Feb. 3, 2015

(54) QUINAZOLINE CARBOXAMIDE AZETIDINES

(75) Inventors: Bayard R. Huck, Sudbury, MA (US); Reinaldo Jones, Lowell, MA (US); Yufang Xiao, Lexington, MA (US); Constantin Neagu, Belmont, MA (US); Donald Bankston, Dracut, MA (US); Andreas Goutopoulos, Boston, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/989,199

(22) PCT Filed: Nov. 11, 2011

(86) PCT No.: PCT/EP2011/005691
§ 371 (c)(1),
(2), (4) Date: May 23, 2013

(87) PCT Pub. No.: WO2012/069146
PCT Pub. Date: May 31, 2012

(65) Prior Publication Data
US 2013/0252942 A1    Sep. 26, 2013

Related U.S. Application Data

(60) Provisional application No. 61/417,131, filed on Nov. 24, 2010.

(51) Int. Cl.
*A61K 31/517* (2006.01)
*C07D 239/72* (2006.01)

(52) U.S. Cl.
USPC .................. 514/266.1; 544/283; 544/284

(58) Field of Classification Search
USPC ........................ 514/266.1; 544/283, 284
See application file for complete search history.

(56) References Cited

U.S. PATENT DOCUMENTS

| 7,799,782 B2 * | 9/2010 | Munson et al. ............ 514/234.5 |
| 8,637,532 B2 * | 1/2014 | Sutton et al. ............... 514/266.1 |
| 2010/0234324 A1 | 9/2010 | Eggenweiler et al. |
| 2012/0046269 A1 | 2/2012 | Sutton et al. |

FOREIGN PATENT DOCUMENTS

| WO | WO-2009 010139 | 1/2009 |
| WO | WO-2010 093419 | 8/2010 |

OTHER PUBLICATIONS

International Search Report for PCT/EP2011/005691, Date of the actual completion of the international search: Dec. 7, 2011, Date of mailing of the international search report: Dec. 16, 2011.

* cited by examiner

*Primary Examiner* — Rei-tsang Shiao
(74) *Attorney, Agent, or Firm* — Millen, White, Zelano & Branigan, P.C.

(57) ABSTRACT

The invention provides novel quinazoline carboxamide azetidine compounds according to Formula (I) and use for the treatment of hyperproliferative diseases, such as cancer.

12 Claims, 1 Drawing Sheet

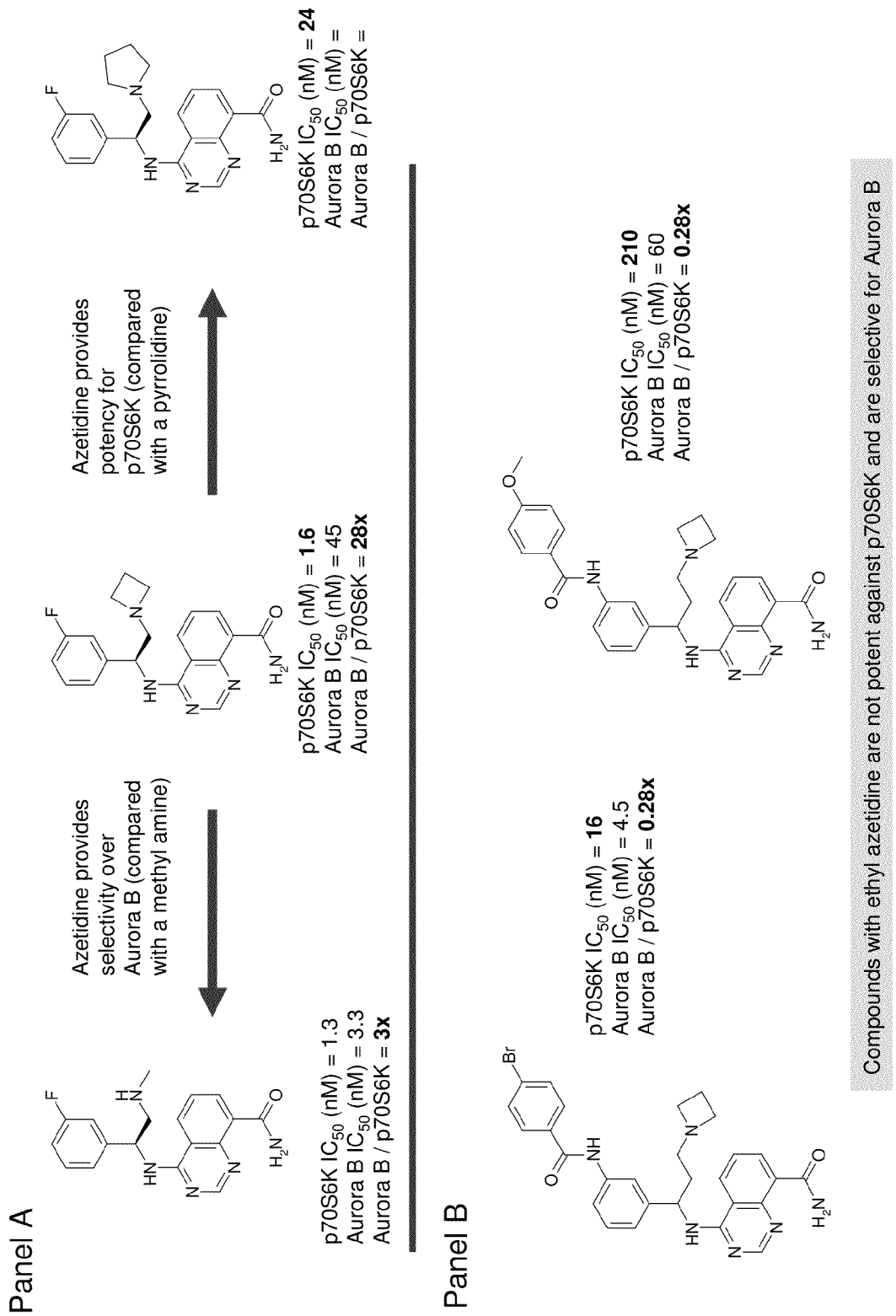

QUINAZOLINE CARBOXAMIDE AZETIDINES

This application is a National Stage entry of PCT/EP2011/005691 filed on Nov. 11, 2011, which claims priority to U.S. Provisional Application Serial No. 61/417,131, filed Nov. 24, 2010.

FIELD OF THE INVENTION

The invention relates to a series of quinazoline carboxamide azetidine compounds that are useful in the treatment of hyperproliferative diseases, such as cancer, in mammals. Also encompassed by the present invention is the use of such compounds in the treatment of hyperproliferative diseases in mammals, especially humans, and pharmaceutical compositions containing such compounds.

SUMMARY OF THE RELATED ART

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)). Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Protein kinase 70S6K, the 70 kDa ribosomal protein kinase p70S6K (also known as SK6, p70/p85 S6 kinase, p70/p85 ribosomal S6 kinase and pp70S6K), is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. p70S6K activity is also under the control of a mTOR-containing complex (TORC1) since rapamycin acts to inhibit p70S6K activity. p70S6K is regulated by PI3K downstream targets AKT and PKCζ. Akt directly phosphorylates and inactivates TSC2, thereby activating mTOR. In addition, studies with mutant alleles of p70S6K that are inhibited by Wortmannin but not by rapamycin suggest that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidime tract at their 5' transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumor metastases, the immune response and tissue repair. Antibodies to p70S6K abolish the mitogenic response driven entry of rat fibroblasts into S phase, indicating that p70S6K function is essential for the progression from G1 to S phase in the cell cycle. Furthermore, inhibition of cell cycle proliferation at the G1 to S phase of the cell cycle by rapamycin has been identified as a consequence of inhibition of the production of the hyperphosphorylated, activated form of p70S6K.

A role for p70S6K in tumor cell proliferation and protection of cells from apoptosis is supported based on its participation in growth factor receptor signal transduction, overexpression and activation in tumor tissues. For example, Northern and Western analyses revealed that amplification of the PS6K gene was accompanied by corresponding increases in mRNA and protein expression, respectively (Cancer Res. (1999) 59: 1408-11-Localization of PS6K to Chromosomal Region 17q23 and Determination of Its Amplification in Breast Cancer).

Chromosome 17q23 is amplified in up to 20% of primary breast tumors, in 87% of breast tumors containing BRCA2 mutations and in 50% of tumors containing BRCA1 mutations, as well as other cancer types such as pancreatic, bladder and neuroblastoma (see M. Barlund, O. Monni, J. Kononen, R. Cornelison, J. Torhorst, G. Sauter, O.-P. Kallioniemi and Kallioniemi A., Cancer Res., 2000, 60:5340-5346). It has been shown that 17q23 amplifications in breast cancer involve the PAT1, RAD51C, PS6K, and SIGMA1B genes (Cancer Res. (2000): 60, pp. 5371-5375). The p70S6K gene has been identified as a target of amplification and overexpression in this region, and statistically significant association between amplification and poor prognosis has been observed.

Clinical inhibition of p70S6K activation was observed in renal carcinoma patients treated with CCI-779 (rapamycin ester), an inhibitor of the upstream kinase mTOR. A significant linear association between disease progression and inhibition of p70S6K activity was reported.

In response to energy stress, the tumor suppressor LKB1 activates AMPK which phosphorylates the TSC1/2 complex and enables it to inactivate the mTOR/p70S6K pathway. Mutations in LKB1 cause Peutz-Jeghers syndrome (PJS), where patients with PJS are 15 times more likely to develop cancer than the general population. In addition, 1/3 of lung adenocarcinomas harbor inactivating LKB1 mutations.

p70S6K has been implicated in metabolic diseases and disorders. It was reported that the absence of p70S6K protects against age- and diet-induced obesity while enhancing insulin sensitivity. A role for p70S6K in metabolic diseases and disorders such as obesity, diabetes, metabolic syndrome, insulin resistance, hyperglycemia, hyperaminoacidemia, and hyperlipidmia is supported based upon the findings.

Compounds described as suitable for p70S6K inhibition are disclosed in WO 03/064397, WO 04/092154, WO 05/054237, WO 05/056014, WO 05/033086, WO 05/117909, WO 05/039506, WO 06/120573, WO 06/136821, WO 06/071819, WO 06/131835, WO 08/140,947 and WO 10/093,419.

In part, aurora kinases modulate a cell's progression through the cell cycle and mitosis. Hallmarks of cancer cell physiology are pathological changes to the normal progression through the cell cycle and mitosis. It has been documented that some compounds which inhibit aurora kinases are also associated with impaired chromosome alignment, weakening of the mitotic checkpoint, polyploidy, and subsequent cell death (Dar et al., Mol Cancer Ther 2010, 9, 268-278). More specifically, inhibition of Aurora B kinase has been shown to cause neutropenia as dose limiting toxicity in several clinical trials (Dar et al., Mol Cancer Ther 2010, 9, 268-278). In addition, inhibition of Aurora B kinase can be an off target effect in ATP competitive kinase inhibitors. These Aurora B kinase inhibitors would also be expected to show neutropenia as dose limiting toxicity caused by aurora inhibition and, therefore, have a limited therapeutic window. Moreover, some aurora kinase inhibitors can also induce polyploidy in normal mammary epithelial cell cultures, thereby, raising the issue of adverse long-term clinical.

Therefore, it is expected that p70S6K inhibitors which substantially spare or significantly reduce the inhibition of Aurora B kinase hold special promise in the treatment of hyperproliferative diseases, such as cancer, by reducing neutropenia as dose limiting toxicity and, thereby, improving the therapeutic window for these compounds.

Furthermore, it is expected that p70S6K inhibitors which also inhibit kinase Akt (upstream of p70S6K in the PI3K pathway) provide more efficient PI3K pathway shutdown (Choo A Y, Yoon S O, Kim S G, Roux P P, Blenis J. Proc. Natl Acad Sci USA. 2008 Nov. 11; 105(45):17414-9.), and allow for capture of any Akt feedback loop activation (Tamburini et al. Blood 2008; 111:379-82).

DESCRIPTION OF THE FIGURES

FIG. 1 documents desirable functional characteristic of a claimed quinazoline carboxamide azetidine compound in comparison to other compounds.

DESCRIPTION OF THE INVENTION

It is the object of the present invention to provide novel p70S6K inhibitors useful in the treatment of hyperproliferative diseases, especially those related to the hyperactivity of the above mentioned protein kinases, such as cancer in mammals, with superior pharmacological properties both with respect to their activities as well as their solubility, metabolic clearance and bioavailability characteristics.

As a result, this invention provides novel quinazoline carboxamide azetidine compounds useful in the treatment of the diseases mentioned herein, that are i) potent p70S6K inhibitors and ii) substantially spare or show significantly reduced Aurora B kinase inhibition as compared to other structurally related quinazoline carboxamide compounds (see FIG. 1).

In a preferred embodiment of the present invention the p70S6K inhibitors are also inhibitors of Akt.

The compounds are defined by Formula (I):

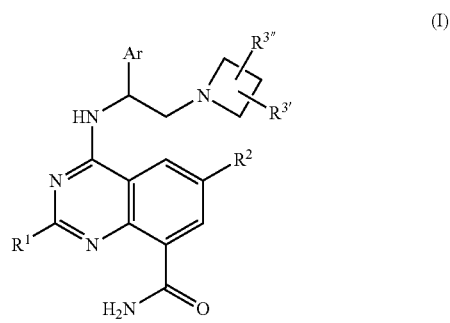

and/or its stereoisomers or tautomers, or pharmaceutically acceptable salts of each of the foregoing, including mixtures thereof in all ratios, wherein:

$R^1$ is H or LA;

$R^2$ is Hal, O(LA), N(LA)(LA)', CONH(LA), Ar, $CONH_2$ or A;

$R^{3'}$, $R^{3''}$ independently are H, LA or Hal,

Ar is a mono- or bicyclic aromatic homo- or heterocycle having 0, 1, 2, 3 or 4 N, O and/or S atoms and 5, 6, 7, 8, 9, or 10 skeleton atoms, which may be unsubstituted or, independently of one another, mono-, di- or trisubstituted by Hal, A, Ar1, OH, SH, OA, O(Ar1), $NH_2$, NHA, NH(Ar1), $NA_2$, $NO_2$, CN, OCN, SCN, COOH, COOA, $CONH_2$, CONHA, CONH(Ar1), $CONA_2$, NHCOA, NHCO(Ar1), NHCONHA, NHCONH(Ar1), $NHCONH_2$, $NHSO_2A$, $NHSO_2$(Ar1), COA, CO(Ar1), $SO_2NH_2$, $SO_2A$, $SO_2$(Ar1) and/or $SO_2Hal$, and in which a ring N-atom may be substituted by an O-atom to form an N-oxide group, and in which in the case of a bicyclic aromatic cycle on of the two rings may be partly saturated, Ar1 is a monocyclic aromatic homo- or heterocycle having 0, 1, 2 or 3 N, O and/or S atoms and 5 or 6 skeleton atoms, which may be unsubstituted or, independently of one another, mono-, di- or trisubstituted by Hal, LA, OH, SH, O(LA), $NH_2$, NH(LA), $N(LA)_2$, $NO_2$, CN, OCN, SCN, COOH, COO(LA), $CONH_2$, CONH(LA), $CON(LA)_2$, NHCO(LA), CHO, CO(LA), $SO_2NH_2$, $SO_2$(LA) and/or $SO_2Hal$, A is unbranched or branched linear or cyclic alkyl having 1, 2, 3, 4, 5, 6, 7 or 8 C atoms, in which one or two $CH_2$ groups may be replaced by an O or S atom and/or by an —NH—, —CO—, —NHCOO—, —NHCONH—. —N(LA)-, —CONH—, —NHCO— or —CH═CH— group, and in which 1-3 H atoms may be replaced by Hal, and in which one or two $CH_3$ groups may be replaced by OH, SH, $NH_2$, NH(LA), $N(LA)_2$, NHCOOH, $NHCONH_2$ or CN, LA is unbranched or branched, linear alkyl having 1, 2, 3 or 4 C atoms, wherein 1, 2 or 3 H atoms may be replaced by Hal, e.g. methyl, ethyl, trifluoromethyl, difluoromethyl, 1,1,1-trifluoroethyl, propyl, isopropyl, butyl, isobutyl, sec-butyl or tert-butyl, and Hal is F, Cl or Br, preferably F or Cl, most preferably F.

A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methyl-propyl, 1,1,2- or 1,2,2-trimethylpropyl.

A further preferably denotes alkyl as defined above, in which one or two CH$_2$ groups may be replaced by O or S atoms and/or by NH, N(LA), CONH, NHCO or —CH=CH— groups and/or in addition 1-3 H atoms may be replaced by F and/or Cl, such as, for example, trifluoromethyl, pentafluoroethyl, 1,1-difluoromethyl, 1,1,1-trifluoroethyl, methoxy, ethoxy, n-propoxy, isopropoxy, n-butoxy, isobutoxy, sec-butoxy or tert-butoxy.

In a preferred embodiment, the novel quinazoline carboxamide azetidine compounds are further defined by Formula (II):

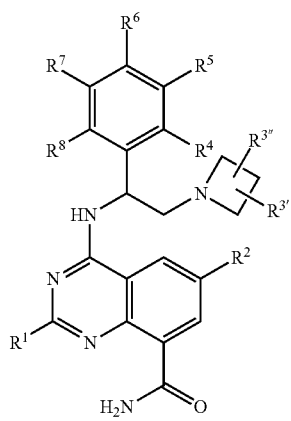

(II)

and/or its stereoisomers or tautomers, or pharmaceutically acceptable salts of each of the foregoing, including mixtures thereof in all ratios, wherein:

R$^4$, R$^5$, R$^6$, R$^7$, R$^8$, independently are H, Hal, LA, OH, SH, O(LA), NH$_2$, NH(LA), N(LA)$_2$, NO$_2$, CN, OCN, SCN, COOH, COO(LA), CONH$_2$, CONH(LA), CON(LA)$_2$, NHCO(LA), NHCONH(LA), NHCONH$_2$, NHSO$_2$(LA), CO(LA), SO$_2$NH$_2$, SO$_2$(LA) or SO$_2$Hal, R$^5$, R$^6$ together with the phenyl group they are attached to, may form a 9 or 10 membered bicyclic ring system, in which 1 or 2 of the non-phenyl carbon atoms may be independently replaced by NH, O or S, in which the cycle formed by R$^5$ and R$^6$ may be unsubstituted or mono- or disubstituted by Hal or LA, One of R$^5$, R$^6$, R'
 may be Ar1, O(Ar1), NH(Ar1), CONH(Ar1), NHCO (Ar1), NHCONH(Ar1), NHSO$_2$(Ar1), CO(Ar1) or SO$_2$ (Ar1),
 while the other two of R$^5$, R$^6$, R' are not Ar1, O(Ar1), NH(Ar1), CONH(Ar1), NHCO(Ar1), NHCONH(Ar1), NHSO$_2$(Ar1), CO(Ar1) or SO$_2$(Ar1), and the remaining substituents have the meanings indicated for Formula (I).

In a more preferred embodiment of Formulae (I) and (II), the stereochemistry at the central chiral carbon atom is as shown in Formulae (I') and (II'):

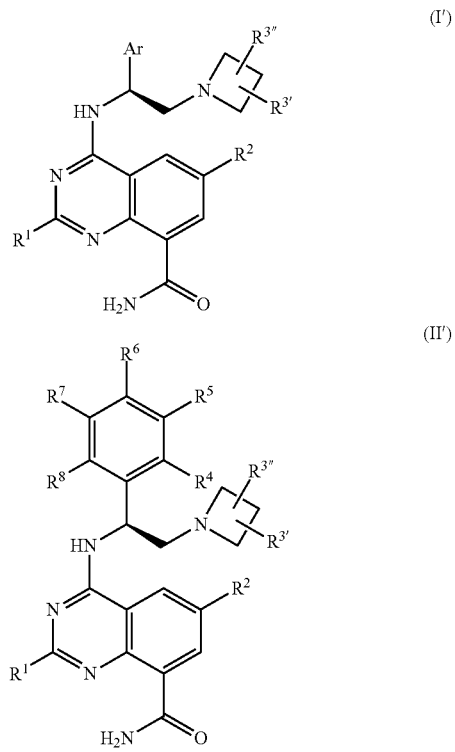

(I')

(II')

In general, all residues which occur more than once may be identical or different, i.e., are independent of one another. Above and below, the residues and parameters have the meanings indicated for Formula (I), Formula (II), Formula (I') and Formula (II") unless expressly indicated otherwise.

Further preferred are compounds of Subformulae 1 to 12 of Formulae (II) and (II'), wherein
in Subformula 1
R$^4$, R$^5$, R$^6$, R$^7$, R$^8$ independently are H, F, Cl, Br, OH, LA, O(LA), CN, C(Hal)$_3$, OC(Hal)$_3$,
in Subformula 2
R$^1$, R$^2$ are H,
in Subformula 3
R$^{3'}$, R$^{3''}$ independently are H, OH or F,
in Subformula 4
R$^4$, R$^8$ independently are H, F or Cl,
in Subformula 5
R$^5$, R$^7$ independently are H, F, Cl, Br, ON, methoxy or CF$_3$,
in Subformula 6
R$^5$, R$^6$ together with the phenyl group they are attached to, form benzo-1,2-dioxolyl, of which the carbon atom bridging the two oxygen atoms may be unsubstituted, or mono- or disubstituted by F or methyl,
in Subformula 7
R$^6$ is H, F, Cl or CF$_3$,
in Subformula 8
R$^5$, R$^6$ independently are H, F, Cl, Br, methyl, CHF$_2$ or CF$_3$,
in Subformula 9
R$^1$, R$^2$, R$^{3'}$, R$^{3''}$, R$^4$, R$^7$, R$^8$ are H,
in Subformula 10
R$^1$, R$^2$, R$^{3'}$, R$^{3''}$, R$^4$, R$^7$, R$^8$ are H, R$^5$, R$^6$ independently are H, F, Cl, Br, methyl, CHF$_2$ or CF$_3$,
in Subformula 11
R$^1$, R$^2$, R$^{3'}$, R$^{3''}$, R$^4$, R$^8$ are H,
R$^5$ is Br, methyl, CHF$_2$ or CF$_3$, $R^6$ is F, Cl or $CF_3$,
$R^7$ is H or F,
in Subformula 12
$R^1$, $R^2$, $R^4$, $R^8$ are H,
$R^{3'}$ is F, or methyl,
$R^{3''}$ is H,
$R^5$ is Br, methyl, $CHF_2$ or $CF_3$,
$R^6$ is F, Cl or $CF_3$,
$R^7$ is H or F,
and the remaining residues have the meaning as indicated for Formula (I).

The compounds of the Formula (I), Formula (II), Formula (I') and Formula (II') may have one or more centres of chirality. They may accordingly occur in various enantiomeric forms and be in racemic or optically active form. The invention therefore also relates to the optically active forms (stereoisomers), the enantiomers, the racemates, and the diastereomers of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3. An elegant method for the resolution of racemates containing ester groups (for example acetyl esters) is the use of enzymes, in particular esterases.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like. If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In cases where the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable solvates" means addition forms with pharmaceutically acceptable solvents that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, e.g. a mono- or dihydrate. If the solvent is alcohol, the solvate formed is an alcoholate, e.g., a methanolate or ethanolate. If the solvent is an ether, the solvate formed is an etherate, e.g., diethyl etherate.

Therefore, the following items are also in accordance with the invention:
 a) all stereoisomers or tautomers of the compounds, including mixtures thereof in all ratios,
 b) prodrugs of the compounds, or stereoisomers or tautomers of these prodrugs,
 c) pharmaceutically acceptable salts of the compounds and of the items mentioned under (a) and (b),
 d) pharmaceutically acceptable solvates of the compounds and of the items mentioned under (a), (b) and (c).

It should be understood that all references to compounds above and below are meant to include these items, in particular pharmaceutically acceptable solvates of the compounds, or pharmaceutically acceptable solvates of their pharmaceutically acceptable salts.

Furthermore, the present invention relates to pharmaceutical compositions comprising compounds of the present invention as an active ingredient, together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other p70S6K inhibitors.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. Preferably, the cancer to be treated is chosen from breast, colorectal, lung, prostate or pancreatic cancer or glioblastoma.

The invention also relates to the use of compounds according to the invention for the preparation of a medicament for the treatment of hyperproliferative diseases related to the hyperactivity of p70S6K as well as diseases modulated by the p70S6K cascade in mammals, or disorders mediated by aberrant proliferation, such as cancer and inflammation.

The invention also relates to a compound or pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier.

In one embodiment, said compound or pharmaceutical composition is for treating a disease selected from the group consisting of tumor angiogenesis, chronic inflammatory disease such as rheumatoid arthritis, inflammatory bowel disease, atherosclerosis; skin diseases such as psoriasis, eczema, and sclerodema; diabetes, obesity, metabolic syndrome, insulin resistance, hyperglycemia, hyperaminoacidemia, hyperlipidmia, diabetic retinopathy, retinopathy of prematurity and age-related macular degeneration.

This invention also relates to a compound or pharmaceutical composition for inhibiting abnormal cell growth/cancer in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth/cancer.

Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of another protein kinase, auch as Akt, Axl, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

This invention further relates to a method for treating cancer in a mammal that comprises administering to the mammal an amount of a compound of the present invention in combination with radiation therapy, wherein the amounts of the compound is in combination with the radiation therapy effective in treating cancer in the mammal. Techniques for administering radiation therapy are known in the art, and these techniques can be used in the combination therapy described herein. The administration of a compound of the invention in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention which amount is effective is sensitizing abnormal cells to treatment with radiation. The amount of the compound in this method can be determined according to the means for ascertaining effective amounts of such compounds described herein. The invention also relates to a method for inhibiting abnormal cell growth in a mammal that comprises an amount of a compound of the present invention or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing the diseases mentioned above and below, for which compounds of the present invention are indicated, generally satisfactory results are obtained when the compounds of the present invention are administered at a daily dosage of from about 0.01 milligram to about 100 milligram per kilogram of animal body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of a) an effective amount of a compound according to the invention, and b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Experimental Section

Some abbreviations that may appear in this application are as follows:

Abbreviations

| Designation | |
|---|---|
| ACN | Acetonitrile |
| ATP | Adenosine triphosphate |
| b | Broad peak |
| cBut | cyclobutyl group |
| cPr | cyclopropyl group |
| d | Doublet |
| DMSO | Dimethylsulfoxide |
| DIEA | N,N-Diisopropylethylamine |
| DTT | Dithiothreitol |
| EDTA | Ethylenediaminetetraacetic acid |
| equiv. | Equivalents |
| Et | Ethyl |
| h | Hour |
| HEPES | 4-(2-hydroxyethyl)-1-piperazineethanesulfonic acid |
| HPLC | High pressure liquid chromatography |

| Designation | |
|---|---|
| iPr | isopropyl group |
| LC/MS | Liquid chromatography coupled to mass spectrometry |
| m | Multiplet |
| M | Molecular ion |
| m/z | Mass-to-charge ratio |
| Me | Methyl |
| min | Minute |
| MS | Mass spectrometry |
| N | Normal (unit of concentration) |
| NMO | 4-methylmorpholine N-oxide |
| NMR | Nuclear Magnetic Resonance |
| PG | Protecting group |
| psi | Pounds per square inch |
| q | Quartette (or quartet) |
| Rf | Retention factor |
| RT | Room temperature |
| Rt. | Retention time |
| s | Singlet |
| Tert | Tertiary |
| TEA | Triethylamine |
| TFA | Trifluoroacetic acid |
| THAB | Tetrahexylammonium bromide |
| THF | Tetrahydrofuran |
| UV | Ultraviolet |
| VIS | Visible |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following schemes and examples. Unless otherwise indicated in the schemes, the variables have the same meaning as described above.

Unless otherwise specified, all starting materials are obtained from commercially suppliers and used without further purifications. Unless otherwise specified, all temperatures are expressed in ° C. and all reactions are conducted at room temperature. Compounds were purified by either silica chromatography or preparative HPLC.

The present invention also relates to processes for manufacturing the compounds of Formula (I) according to the hereinafter described schemes and working examples.

General Synthetic Schemes

Scheme 1.
Amino alcohol hydrochloride was treated with di-tertbutyl dicarbonate in the presence of 2N sodium hydroxide and t-butanol as solvent to afford the Boc-protected amino alcohol A. Cyclization with thionyl chloride to the sulfoxide intermediate was followed by in oxidation with sodium periodate in the presence of ruthenium catalyst to provide the cyclic intermediate B. Nucleophilic attack of B with an azetidine moiety and in-situ Boc deprotection with hydrochloric acid/methanol afforded the desired amine di*hydrochloride salt intermediate C.

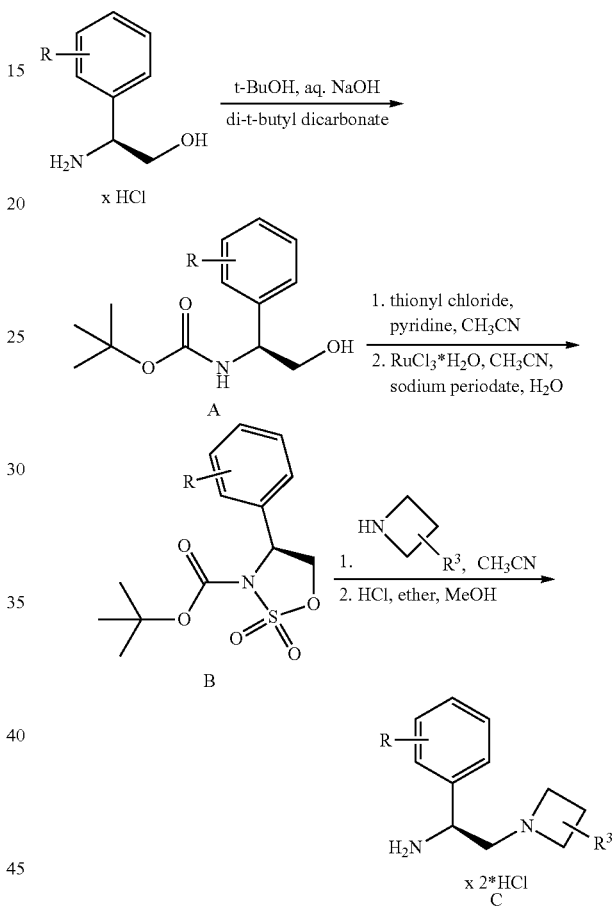

Scheme 2.
Refluxing substituted 2-aminoisophthalic acid was treated with formaldehyde at 185° C. for 4 hours. Subsequent treatment with concentrated ammonium hydroxide afforded a quinazoline carboxylic acid intermediate. Esterification with methanol and sulfuric acid under refluxing conditions afforded the methyl ester which was converted to the 4-chloro-quinazoline carboxylic acid methyl ester D upon treatment with phosphorous oxychloride and DIEA in the presence of a phase transfer catalyst.

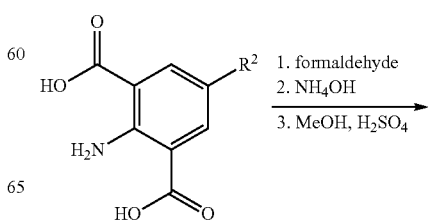

-continued

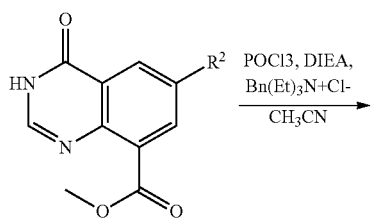

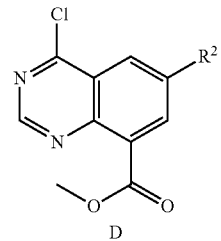

Scheme 3.
4-Chloro quinazoline derivative D was reacted with amine di*hydrochloride salt intermediate C in the presence of Hunig's base to provide the quinazoline methyl ester intermediate. Ammonolysis of the ester group with 7N ammonia/methanol solution afforded carboxamide E.

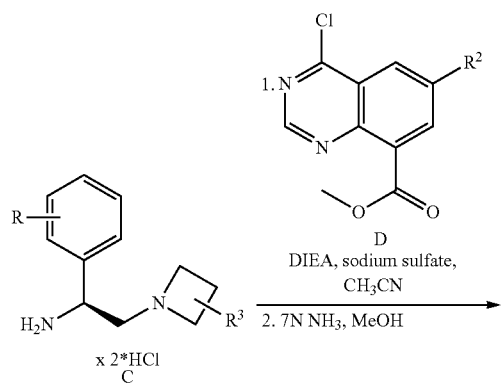

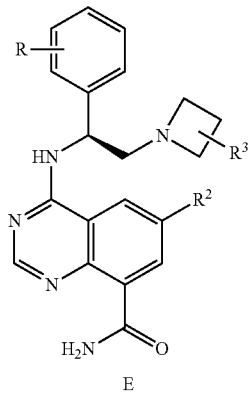

Accordingly, the present invention also relates to a process for the manufacture of compounds of Formula (I), wherein LG is a leaving group, and the remaining substituents have the meaning as defined for Formula (I), wherein a compound of Formula (V)

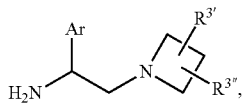

is reacted with a compound of Formula (IV)

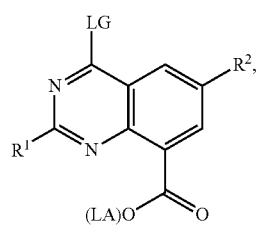

to yield a carboxylic ester compound of Formula (III),

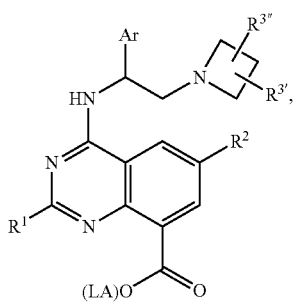

which is then converted to a carboxamide compound of Formula (I). Preferably, LA is methyl, ethyl, isopropyl or tert-butyl, most preferably methyl. Suitable leaving groups are, for example, Cl, Br, I, mesylate, tosylate, phenylsulfonate or trifluoroacetate. Preferably LG is Cl.

Synthesis In Detail

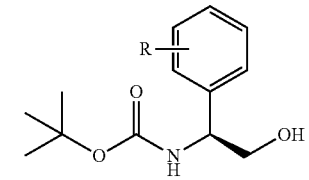

Boc-Protected Amino Alcohol (A)

A mixture of the amino alcohol hydrochloride (192.22 mmol) and di-t-butyl dicarbonate (262.63 mmol, 1.37 eq) was suspended in t-BuOH (250 mL, 6.25 volumes) and then treated with aqueous 2 N NaOH (120 mL, 240 mmol). The contents were warmed to 75° C. (immediate effervescence was observed) for 4 h. The internal temp was then reduced to 50° C., and the contents were added to water (2 L) with vigorous stirring. After 15 min, a pure, white solid (A) precipitated, and the contents were cooled to 5° C., prior to filtration. The collected solid was washed with water (0.5 L) and dried under vacuum at 35° C. for 18 h (90-99% yield).

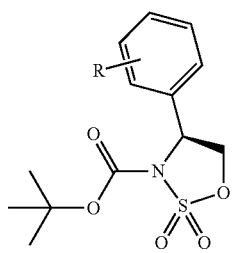

Cyclic Sulfone (B)

A solution of thionyl chloride (184.42 mmol, 2.5 eq) in CH$_3$CN (25 mL) was cooled to −40° C., prior to dropwise addition of A (73.60 mmol) in CH$_3$CN (100 mL). The internal temperature was maintained at −40° C. during the addition. Pyridine (372.94 mmol, 5 eq) was then added, and the thick suspension was allowed to slowly warm to room temperature (over 2-3 h). The contents became a yellow solution that eventually became a shade of green. At that time, the contents were concentrated to a green or yellow residue, which was suspended in EtOAc (200 mL) and filtered over a plug of silica gel (250 cc, equilibrated in EtOAc). The filtration was continued until UV-active material was no longer detected. The resultant filtrate (~700 mL) was concentrated, and again concentrated from CH$_3$CN (2×50 mL) and dried under vacuum for 16 h to remove residual pyridine. The resultant yellow solid was dissolved in CH$_3$CN (170 mL), treated with ruthenium(III) chloride hydrate (8.0 mmol, 0.11 eq), followed by sodium periodate (88.32 mmol, 1.2 eq), and H$_2$O (170 mL). The dark solution was stirred at room temperature for 18 h. At that time, the contents were diluted with EtOAc (300 mL) and H$_2$O (300 mL), and the layers were separated. The organics were dried over sodium sulfate, concentrated via rotary evaporation and dried under vacuum for 16 h to afford B as a tan solid (82-89%). A second extraction did not afford additional product.

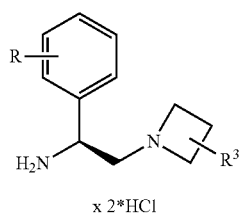

Azetidine Phenylethanamine Dihydrochloride (C)

A suspension of B (52.52 mmol) in CH$_3$CN (100 mL) was treated with azetidine (65.67 mmol, 1.25 eq), and the contents were stirred at room temp for 30-60 minutes. A solid precipitated, which was filtered, washed with MeOH or acetone (100 mL) and dried under vacuum for 2 hours to provide the Boc-protected azetidine phenylethanamine intermediate (60-77%) as a white solid.

A suspension of the Boc-protected azetidine phenylethanamine intermediate (38.61 mmol) in anhydrous MeOH (50 mL) was treated with 2.0 M HCl in diethyl ether (200 mmol, ~5 eq), and the contents were stirred at room temperature. Dissolution occurred, followed by precipitation of a solid. After 3 hours, the solid was collected by filtration, washed with diethyl ether (100 mL) and dried under vacuum for 2 hours to afford C as a white or off-white solid (69-75%).

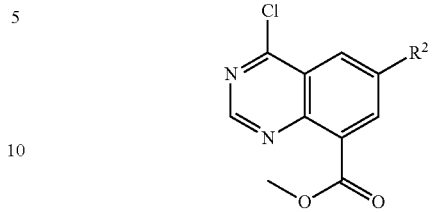

4-chloroquinazoline-8-carboxylate (D)

4-oxo-4H-3,1-benzoxazine-8-carboxylic acid

2-Aminoisophthalic acid moiety (50.0 g; 276.0 mmol) and formaldehyde (250.0 ml; 5.00 V) were combined and heated to 140° C. for 4 h. The reaction mixture was cooled to room temperature and distilled under high vacuum on the rotary evaporator. The remaining formaldehyde was removed by azeotropic distillation with toluene. The residue was slurried with ethyl ether, filtered, and the solid was dried under vacuum to provide the desired intermediate (50.3 g, 89% yield).

4-oxo-3,4-dihydroquinazoline-8-carboxylic acid 4-oxo-4H-3,1-benzoxazine-8-carboxylic acid derivative (51.5 g; 251.26 mmol) was dissolved in NH$_4$OH (360.0 ml; 6.98 V; 28% solution). Ammonium acetate (77.5 g; 1.005 mmol) was added, and the reaction mixture was heated at 80° C. for 2 h. The reaction mixture was cooled to room temperature and diluted with MeOH (40 mL) then heated for 72 h at 80° C. in a pressure bottle. The reaction mixture was concentrated on the rotary evaporator then cooled on ice and filtered. The solid was dried under vacuum to provide the desired product (33.5 g, 65% yield).

Methyl 4-oxo-3,4-dihydroquinazoline-8-carboxylate 4-oxo-3,4-dihydroquinazoline-8-carboxylic acid derivative (28.2 g; 138.11 mmol) was dissolved in dry MeOH (1000 mL). Sulfuric acid (29.4 ml; 552.44 mmol) was added dropwise to the reaction mixture under argon. The reaction mixture was refluxed overnight, cooled to room temperature, and then concentrated. The solid was filtered and dried under vacuum to provide the desired intermediate as a sulfate salt.

The sulfate salt (40.6 g, 128.36 mmol) was treated with K$_2$CO$_3$ (8.87 g, 64.18 mmol) in H$_2$O (100 mL). Upon dissolution, an off-white precipitate was formed. Additional H$_2$O (100 mL) was added, and the pH was adjusted between 6 and 7. The off-white solid was filtered, washed with H$_2$O (150 mL), and dried under vacuum to provide the desired intermediate (17.90 g, 64% yield). The aqueous layer was extracted with EtOAc (250 mL) to provide another 1.10 g (4% yield).

Methyl 4-chloro-2-methylquinazoline-8-carboxylate

A suspension of methyl 4-oxo-3,4-dihydroquinazoline-8-carboxylate (48.97 mmol) and benzyltriethylammonium chloride (195.99 mmol) in dry CH$_3$CN (25 mL) was treated with DIEA (9 mL, 6.68 g, 51.68 mmol) and stirred as POCl$_3$ (40 mL, 65.80 g, 429.14 mmol) was slowly added to the flask. The contents were warmed to 90° C. for 30 min, cooled to ~50° C., and slowly poured into aqueous 2 N NaOH (400 mL, 1600 mmol) and water (400 mL) that was cooling in an acetone/dry-ice bath (ice formed in the flask). The off-white solid that precipitated was filtered, washed with 10% aqueous K$_2$CO$_3$ (100 mL), and the resultant cake was dried under vacuum at 35° C. for 19 h, to provide D as a off-white solid (8.10 g, 36.38 mmol, 74%).

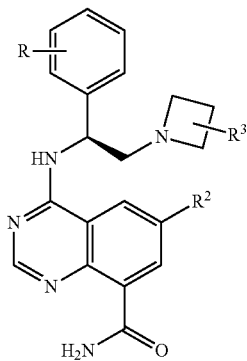

Quinazoline Carboxamide Azetidine (E)

A suspension of C (17.63 mmol) and sodium sulfate (52.89 mmol, 3 eq) in CH$_3$CN (10V) was treated with DIEA (105.77 mmol, 6 eq), and the contents were stirred for 10 minutes, prior to addition of D (17.63 mmol, 1 eq). Stirring was continued for 2-3 hours at 45-60° C., and MeOH (20 mL) was added to the flask to quench the reaction. The contents were concentrated to dryness, and again concentrated from MeOH (3×100 mL). The resultant residue was dissolved in MeOH (20 mL) and transferred to a pressure vessel. The contents of the pressure vessel were concentrated to dryness, prior to addition of 7 N NH$_3$ in MeOH (100 mL). The contents were then warmed to 60° C., and stirring was continued for 18 hours. At that time, the contents were concentrated to a residue that was suspended in EtOAc. The organics were washed with water. The water layer was repeatedly extracted with EtOAc until the entire compound was in the organic layer. The combined organics were dried over sodium sulfate and concentrated. The resultant residue was further purified by precipitation from MeOH or mixtures of MeOH/acetone (30-50%).

Analytical Methodology
Analytical LC/MS was Performed Using the Following Three Methods:

Method A:
A Discovery C$^{18}$, 5 μm, 3×30 mm column was used at a flow rate of 400 μL/min, sample loop 5 μL, mobile phase: (A) water with 0.1% formic acid, mobile phase, (B) methanol with 0.1% formic acid; retention times are given in minutes. Method details: (I) runs on a Quaternary Pump G1311A (Agilent) with UV/VIS diode array detector G1315B (Agilent) and Finnigan LCQ Duo MS detector in ESI+ modus with UV-detection at 254 and 280 nm with a gradient of 15-95% (B) in a 3.2 min linear gradient (II) hold for 1.4 min at 95% (B) (III) decrease from 95-15% (B) in a 0.1 min linear gradient (IV) hold for 2.3 min at 15% (B).

Method B:
A Waters Symmetry C$^{18}$, 3.5 μm, 4.6×75 mm column at a flow rate of 1 mL/min, sample loop 10 μL, mobile phase (A) is water with 0.05% TFA, mobile phase (B) is ACN with 0.05% TFA; retention times are given in minutes. Methods details: (I) runs on a Binary Pump G1312A (Agilent) with UV/Vis diode array detector G1315B (Agilent) and Agilent G1956B (SL) MS detector in ESI+ mode with UV-detection at 254 and 280 nm with a gradient of 20-85% (B) in a 10 min linear gradient (II) hold for 1 min at 85% (B) (III) decrease from 20-85% (B) in a 0.2 min linear gradient (IV) hold for 3.8 min at 20% (B).

Method C:
Gradient: 4.2 min/Flow: 2 ml/min 99:01-0:100 Water+ 0.1% (Vol.) TFA; Acetonitril+0.1% (Vol.) TFA; 0.0 to 0.2 min: 99:01; 0.2 to 3.8 min: 99:01→0:100; 3.8 to 4.2 min: 0:100; Column: Chromolith Performance RP18e; 100 mm long, 3 mm diameter; Wavelength: 220 nm.

Analytical Chiral HPLC
Analytical chiral HPLC was performed using a ChiralPak AD-H column (250×4.6 mm) from Daicel Chemical Industries, Ltd. on an Agilent 1100 Series system. The method used a 5.0 μL injection volume, with a flow rate of 1 mL/min of 100% methanol for 15 min at 25° C., and UV-detection at 254 and 280 nm.

Preparative HPLC
Preparative HPLC was performed using either a Waters Atlantis dC$_{18}$ OBD™ 10 μM (30×250 mm) column or a Waters Sunfire Prep C$_{18}$ OBD 10 μM (30×250 mm) column. The columns were used at a flow rate of 60 mL/min on a Waters Prep LC 4000 System equipped with a sample loop (10 mL) and an ISCO UA-6 UV/Vis detector. The mobile phase was drawn from two solvent reservoirs containing (A) water and (B) HPLC-grade acetonitrile. A typical preparative run used a linear gradient (e.g., 0-60% solvent B over 60 min).

EXAMPLES

The working examples presented below are intended to illustrate particular embodiments of the invention, and are not intended to limit the scope of the specification or the claims in any way.

Example Compounds According to Formula (I)

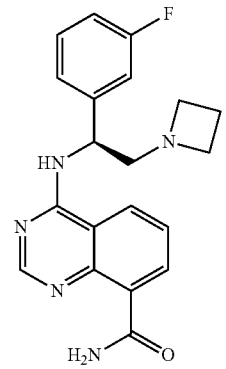

4-[(S)-2-Azetidin-1-yl-1-(3-fluorophenyl)-ethylamino]-quinazoline-8-carboxylic acid amide (1)

IC$_{50}$ p70S6K [nM]: 5.6
pS6 MDA-MB-468 [nM]: 70
Akt1 IC$_{50}$ [nM]: 22
Aurora B IC$_{50}$ [nM]: 45
Aurora B/p70S6K inhibitory ratio: 28

Example 1 was prepared following the general synthesis of A-E starting with (S)-2-amino-2-(3-fluoro-phenyl)-ethanol. LC-MS [366 (M+1)]

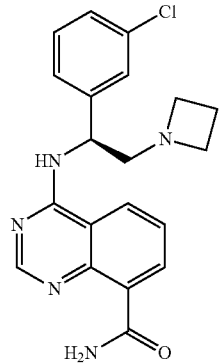 [SMILES: NC(=O)c1cccc2c(N[C@H](CN3CCC3)c3cccc(Cl)c3)ncnc12]

4-[(S)-2-Azetidin-1-yl-1-(3-chlorophenyl)-ethylamino]-quinazoline-8-carboxylic acid amide (2)

IC$_{50}$ p70S6K [nM]: 1.1
pS6 MDA-MB-468 [nM]: 16
Akt1 IC$_{50}$ [nM]: 10
Aurora B IC$_{50}$ [nM]: 47

Example 2 was prepared following the general synthesis of A-E starting with (S)-2-amino-2-(3-chloro-phenyl)-ethanol. LCMS [381.9 (M+1)]. $^1$H NMR (DMSO-d$_6$, ppm) 1.91 (2H), 2.75 (1H), 2.95 (1H), 3.15 (4H), 5.43 (1H), 7.30 (2H), 7.50 (1H), 7.68 (1H), 7.79 (1H), 7.98 (1H), 8.53 (1H), 8.54 (2H), 8.58 (1H), 10.30 (1H).

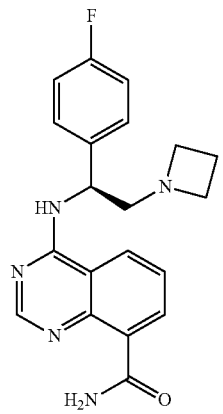 [SMILES: NC(=O)c1cccc2c(N[C@H](CN3CCC3)c3ccc(F)cc3)ncnc12]

4-[(S)-2-Azetidin-1-yl-1-(4-fluorophenyl)-ethylamino]-quinazoline-8-carboxylic acid amide (3)

IC$_{50}$ p70S6K [nM]: 7.8
pS6 MDA-MB-468 [nM]: 103
Akt1 IC$_{50}$ [nM]: 23
Aurora B IC$_{50}$ [nM]: 41

Example 3 was prepared following the general synthesis of A-E starting with (S)-2-amino-2-(4-fluoro-phenyl)-ethanol. LCMS [366.2 (M+1)]. $^1$H NMR (DMSO-d$_6$, ppm) 1.92 (2H), 2.71 (1H), 2.99 (1H), 3.14 (4H), 5.44 (1H), 7.14 (2H), 7.49 (2H), 7.67 (1H), 7.83 (1H), 8.53 (1H), 8.57 (1H), 8.73 (2H), 10.34 (1H).

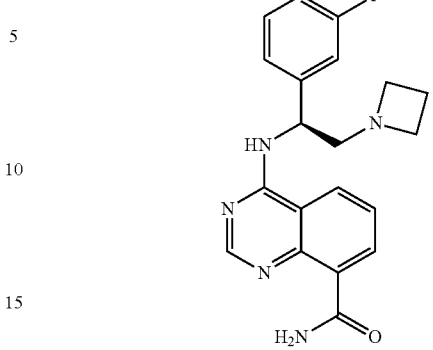

4-[(S)-2-Azetidin-1-yl-1-(3,4-difluorophenyl)-ethylamino]-quinazoline-8-carboxylic acid amide (4)

IC$_{50}$ p70S6K [nM]: 1.2
pS6 MDA-MB-468 [nM]: 74
Akt1 IC$_{50}$ [nM]: 4.1
Aurora B IC$_{50}$ [nM]: 56

Example 4 was prepared following the general synthesis of A-E starting with (S)-2-amino-2-(3,4-di-fluoro-phenyl)-ethanol. LCMS [384.20 (M+1)]. $^1$H NMR (DMSO-d$_6$, ppm) 1.92 (2H), 2.75 (1H), 2.93 (1H), 3.15 (4H), 5.43 (1H), 7.34 (2H), 7.53 (1H), 7.68 (1H), 7.81 (1H), 8.58 (4H), 10.30 (1H).

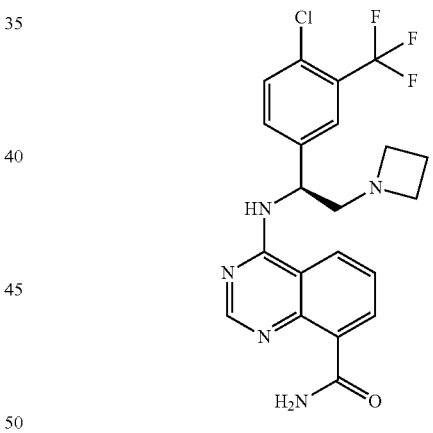

4-[(S)-2-Azetidin-1-yl-1-(4-chloro-3-trifluoromethylphenyl)-ethylamino]-quinazoline-8-carboxylic acid amide (5)

IC$_{50}$ p70S6K [nM]: 0.9
pS6 MDA-MB-468 [nM]: 11
Akt1 IC$_{50}$ [nM]: 1.4
Aurora B IC$_{50}$ [nM]: 100

Example 5 was prepared following the general synthesis of A-E starting with (S)-2-amino-2-(4-chloro-3-trifluoromethyl-phenyl)-ethanol. LCMS [450.10 (M+1)]. $^1$H NMR (DMSO-d$_6$, ppm) 1.92 (2H), 2.74 (1H), 2.94 (1H), 3.15 (4H), 5.45 (1H), 7.67 (2H), 7.76 (1H), 7.78 (1H), 7.79 (1H), 8.54 (3H), 8.75 (1H), 10.27 (1H).

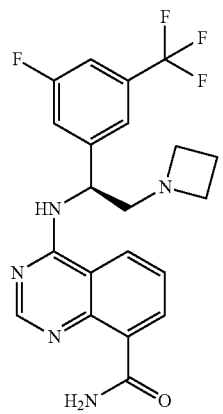 [SMILES: NC(=O)c1cccc2c(N[C@H](CN3CCC3)c3cc(F)cc(C(F)(F)F)c3)ncnc12]

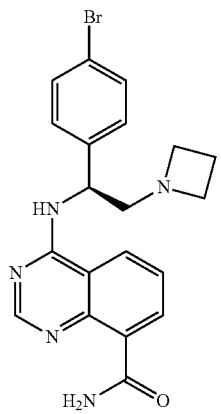

4-[(S)-2-Azetidin-1-yl-1-(3-fluoro-5-trifluoromethylphenyl)-ethylamino]-quinazoline-8-carboxylic acid amide (6)

IC$_{50}$ p70S6K [nM]: 2.3
pS6 MDA-MB-468 [nM]: 98
Akt1 IC$_{50}$ [nM]: 9.1
Aurora B IC$_{50}$ [nM]: 270

Example 6 was prepared following the general synthesis of A-E starting with (S)-2-amino-2-(3-fluoro-5-trifluoromethyl-phenyl)-ethanol. LCMS [434.20 (M+1)]. $^1$H NMR (DMSO-d$_6$, ppm) 1.92 (2H), 2.73 (1H), 2.93 (1H), 3.19 (4H), 5.51 (1H), 7.51 (1H), 7.70 (2H), 7.82 (1H), 8.54 (3H), 8.73 (1H), 10.27 (1H).

4-[(S)-2-Azetidin-1-yl-1-(4-bromophenyl)-ethylamino]-quinazoline-8-carboxylic acid amide (8)

IC$_{50}$ p70S6K [nM]: 1.6
pS6 MDA-MB-468 [nM]: 39
Akt1 IC$_{50}$ [nM]: 48
Aurora B IC$_{50}$ [nM]: 65

Example 8 was prepared following the general synthesis of A-E starting with (S)-2-amino-2-(4-bromo-phenyl)-ethanol. LCMS [427.10 (M+1)].

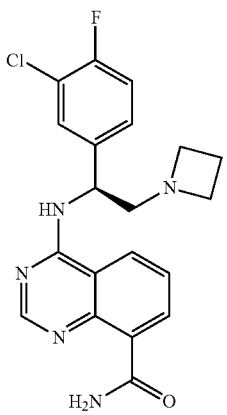 [SMILES: NC(=O)c1cccc2c(N[C@H](CN3CCC3)c3ccc(F)c(Cl)c3)ncnc12]

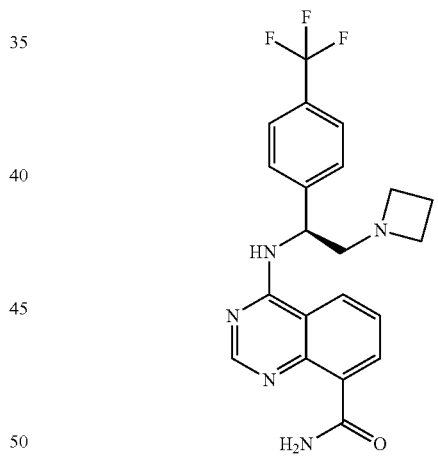

4-[(S)-2-Azetidin-1-yl-1-(3-chloro-4-fluorophenyl)-ethylamino]-quinazoline-8-carboxylic acid amide (7)

IC$_{50}$ p70S6K [nM]: 1.3
pS6 MDA-MB-468 [nM]: 1.3
Akt1 IC$_{50}$ [nM]: 12
Aurora B IC$_{50}$ [nM]: 58

Example 7 was prepared following the general synthesis of A-E starting with (S)-2-amino-2-(3-chloro-4-fluoro-phenyl)-ethanol. LCMS [400.10 (M+1)]. $^1$H NMR (DMSO-d$_6$, ppm) 1.91 (2H), 2.72 (1H), 2.94 (1H), 3.16 (4H), 5.41 (1H), 7.38 (1H), 7.47 (1H), 7.68 (2H), 7.81 (1H), 8.58 (4H), 10.29 (1H).

4-[(S)-2-Azetidin-1-yl-1-(4-trifluoromethylphenyl)-ethylamino]-quinazoline-8-carboxylic acid amide (9)

IC$_{50}$ p70S6K [nM]: 0.8
pS6 MDA-MB-468 [nM]: 10.0
Akt1 IC$_{50}$ [nM]: 17
Aurora B IC$_{50}$ [nM]: 260

Example 9 was prepared following the general synthesis of A-E starting with (S)-2-amino-2-(4-trifluoromethyl-phenyl)-ethanol. LCMS [416.15 (M+1)].

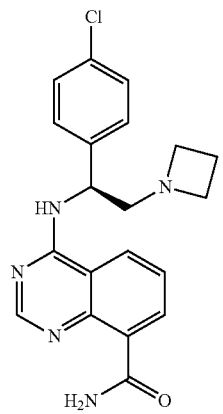 [SMILES: NC(=O)c1cccc2c(N[C@H](CN3CCC3)c3ccc(Cl)cc3)ncnc12]

4-[(S)-2-Azetidin-1-yl-1-(4-chlorophenyl)-ethylamino]-quinazoline-8-carboxylic acid amide (10)

IC$_{50}$ p70S6K [nM]: 1
pS6 MDA-MB-468 [nM]: 36
Akt1 IC$_{50}$ [nM]: 21
Aurora B IC$_{50}$ [nM]: 43

Example 10 was prepared following the general synthesis of A-E starting with (S)-2-amino-2-(4-chloro-phenyl)-ethanol. LCMS [382.20 (M+1)]. $^1$H NMR (DMSO-d$_6$, ppm) 1.91 (2H), 2.71 (1H), 2.96 (1H), 3.15 (4H), 5.40 (1H), 7.36 (2H), 7.46 (2H), 7.67 (1H), 7.79 (1H), 8.51 (1H), 8.57 (1H), 8.62 (2H), 10.30 (1H).

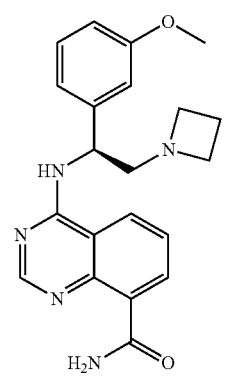

4-[(S)-2-Azetidin-1-yl-1-(3-methoxyphenyl)-ethylamino]-quinazoline-8-carboxylic acid amide (12)

IC$_{50}$ p70S6K [nM]: 4.4
pS6 MDA-MB-468 [nM]: 204
Akt1 IC$_{50}$ [nM]: 250
Aurora B IC$_{50}$ [nM]: 67

Example 12 was prepared following the general synthesis of A-E starting with (S)-2-amino-2-(3-methoxy-phenyl)-ethanol. LCMS [373.20 (M+1)]. $^1$H NMR (DMSO-d$_6$, ppm) 1.92 (2H), 2.69 (1H), 2.98 (1H), 3.16 (4H), 3.72 (3H), 5.44 (1H), 6.81 (1H), 7.03 (2H), 7.23 (1H), 7.66 (1H), 7.83 (1H), 8.52 (2H), 8.67 (2H), 10.34 (1H).

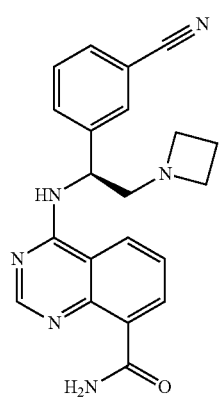 [SMILES: N#Cc1cccc([C@@H](CN2CCC2)Nc2ncnc3c(C(N)=O)cccc23)c1]

4-[(S)-2-Azetidin-1-yl-1-(3-cyanophenyl)-ethylamino]-quinazoline-8-carboxylic acid amide (11)

IC$_{50}$ p70S6K [nM]: 3.3
pS6 MDA-MB-468 [nM]: 382
Akt1 IC$_{50}$ [nM]: 270
Aurora B IC$_{50}$ [nM]: 690

Example 11 was prepared following the general synthesis of A-E starting with 3-((S)-1-amino-2-hydroxy-ethyl)-benzonitrile. LCMS [373.20 (M+1)]. $^1$H NMR (DMSO-d$_6$, ppm) 1.9200 (2H), 2.7371 (1H), 2.9724 (1H), 3.1720 (4H), 5.4625 (1H), 7.5225 (1H), 7.7136 (2H), 7.7961 (2H), 7.9454 (1H), 8.5327 (1H), 8.5828 (1H), 8.6154 (1H), 8.7316 (1H), 10.2982 (1H).

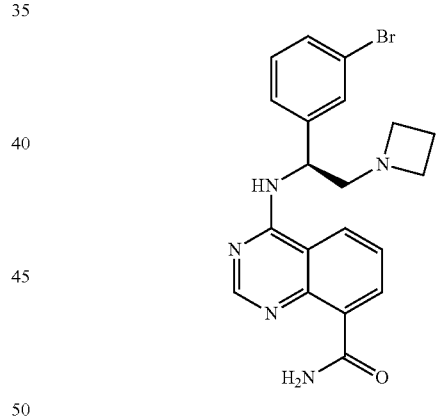

4-[(S)-2-Azetidin-1-yl-1-(3-bromophenyl)-ethylamino]-quinazoline-8-carboxylic acid amide (13)

IC$_{50}$ p70S6K [nM]: 0.3
pS6 MDA-MB-468 [nM]: 25.0
Akt1 IC$_{50}$ [nM]: 5
Aurora B IC$_{50}$ [nM]: 17

Example 13 was prepared following the general synthesis of A-E starting with (S)-2-amino-2-(3-bromo-phenyl)-ethanol. LCMS [427.10 (M+1)]. $^1$H NMR (DMSO-d$_6$, ppm) 1.91 (2H), 2.75 (1H), 2.97 (1H), 3.15 (4H), 5.41 (1H), 7.25 (1H), 7.45 (2H), 7.67 (2H), 7.84 (1H), 8.53 (1H), 8.54 (1H), 8.61 (1H), 8.63 (1H), 10.31 (1H).

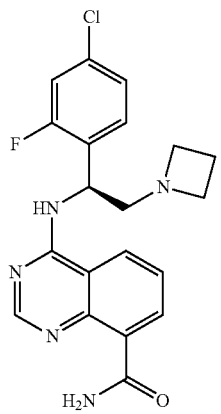 [SMILES: NC(=O)c1cccc2c(N[C@H](CN3CCC3)c3ccc(Cl)cc3F)ncnc12]

4-[(S)-2-Azetidin-1-yl-1-(2-fluoro-4-chlorophenyl)-ethylamino]-quinazoline-8-carboxylic acid amide (14)

IC$_{50}$ p70S6K [nM]: 1.1
pS6 MDA-MB-468 [nM]: 86.0
Akt1 IC$_{50}$ [nM]: 25
Aurora B IC$_{50}$ [nM]: 69

Example 14 was prepared following the general synthesis of A-E starting with (S)-2-amino-2-(4-chloro-2-fluoro-phenyl)-ethanol. LCMS [400.10 (M+1)]. $^1$H NMR (DMSO-d$_6$, ppm) 1.93 (2H), 2.71 (1H), 2.99 (1H), 3.15 (4H), 5.62 (1H), 7.23 (1H), 7.39 (1H), 7.54 (1H), 7.68 (1H), 7.82 (1H), 8.53 (1H), 8.58 (1H), 8.69 (2H), 10.27 (1H).

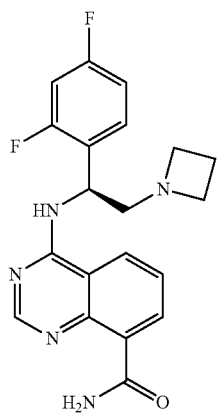

4-[(S)-2-Azetidin-1-yl-1-(2,4-difluorophenyl)-ethylamino]-quinazoline-8-carboxylic acid amide (15)

IC$_{50}$ p70S6K [nM]: 6
pS6 MDA-MB-468 [nM]: 144
Akt1 IC$_{50}$ [nM]: 84
Aurora B IC$_{50}$ [nM]: 200

Example 15 was prepared following the general synthesis of A-E starting with (S)-2-amino-2-(2,4-di-fluoro-phenyl)-ethanol. LCMS [384.20 (M+1)]. $^1$H NMR (DMSO-d$_6$, ppm) 1.92 (2H), 2.69 (1H), 2.99 (1H), 3.17 (4H), 5.66 (1H), 7.04 (1H), 7.21 (1H), 7.56 (1H), 7.69 (1H), 7.84 (1H), 8.53 (1H), 8.53 (1H), 8.63 (2H), 10.29 (1H).

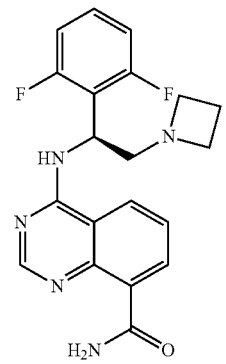 [SMILES: NC(=O)c1cccc2c(N[C@H](CN3CCC3)c3c(F)cccc3F)ncnc12]

4-[(S)-2-Azetidin-1-yl-1-(2,6-difluorophenyl)-ethylamino]-quinazoline-8-carboxylic acid amide (16)

IC$_{50}$ p70S6K [nM]: 5.4
pS6 MDA-MB-468 [nM]: 183
Akt1 IC$_{50}$ [nM]: 91
Aurora B IC$_{50}$ [nM]: 170

Example 16 was prepared following the general synthesis of A-E starting with (S)-2-amino-2-(2,6-di-fluoro-phenyl)-ethanol. LCMS [384.20 (M+1)]. $^1$H NMR (DMSO-d$_6$, ppm) 1.92 (2H), 2.69 (1H), 2.99 (1H), 3.17 (4H), 5.65 (1H), 7.01 (2H), 7.31 (1H), 7.66 (1H), 7.83 (1H), 8.53 (1H), 8.56 (1H), 8.71 (2H), 10.27 (1H).

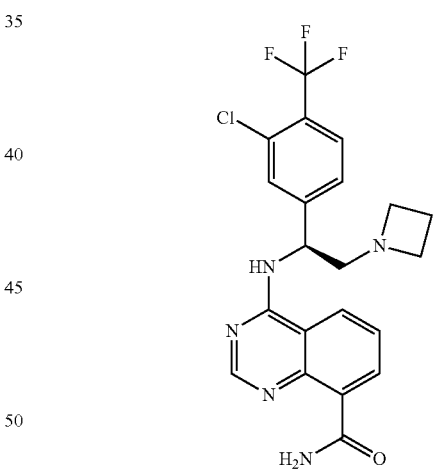

4-[(S)-2-Azetidin-1-yl-1-(3-chloro-4-trifluoromethylphenyl)-ethylamino]-quinazoline-8-carboxylic acid amide (17)

IC$_{50}$ p70S6K [nM]: 2.3
pS6 MDA-MB-468 [nM]: 8
Akt1 IC$_{50}$ [nM]: 3.7
Aurora B IC$_{50}$ [nM]: 130

Example 17 was prepared following the general synthesis of A-E starting with (S)-2-amino-2-(3-chloro-4-trifluoromethyl-phenyl)-ethanol. LCMS [450.10 (M+1)].

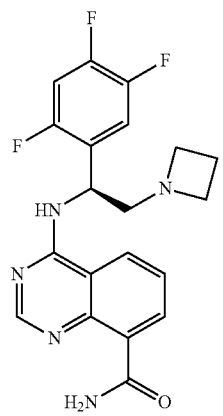 [SMILES: NC(=O)c1cccc2c(N[C@H](CN3CCC3)c3cc(F)c(F)cc3F)ncnc12]

4-[(S)-2-Azetidin-1-yl-1-(2,4,5-trifluorophenyl)-ethylamino]-quinazoline-8-carboxylic acid amide (18)

IC$_{50}$ p70S6K [nM]: 3.8
pS6 MDA-MB-468 [nM]: 85.0
Akt1 IC$_{50}$ [nM]: 36
Aurora B IC$_{50}$ [nM]: 220

Example 18 was prepared following the general synthesis of A-E starting with (S)-2-amino-2-(2,4,5-tri-fluoro-phenyl)-ethanol. LCMS [384.20 (M+1)]. $^1$H NMR (DMSO-d$_6$, ppm) 1.93 (2H), 2.72 (1H), 2.96 (1H), 3.17 (4H), 5.66 (1H), 7.55 (1H), 7.69 (1H), 7.70 (1H), 7.85 (1H), 8.55 (1H), 8.56 (2H), 10.28 (1H).

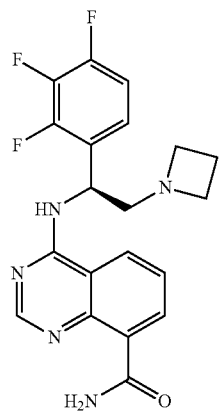 [SMILES: NC(=O)c1cccc2c(N[C@H](CN3CCC3)c3ccc(F)c(F)c3F)ncnc12]

4-[(S)-2-Azetidin-1-yl-1-(2,3,4-trifluorophenyl)-ethylamino]-quinazoline-8-carboxylic acid amide (19)

IC$_{50}$ p70S6K [nM]: 2.1
pS6 MDA-MB-468 [nM]: 62.0
Akt1 IC$_{50}$ [nM]: 23
Aurora B IC$_{50}$ [nM]: 360

Example 19 was prepared following the general synthesis of A-E starting with (S)-2-amino-2-(2,3,4-tri-fluoro-phenyl)-ethanol. LCMS [384.20 (M+1)]. $^1$H NMR (DMSO-d$_6$, ppm) 1.91 (2H), 2.75 (1H), 2.99 (1H), 3.16 (4H), 5.66 (1H), 7.26 (1H), 7.37 (1H), 7.77 (1H), 7.84 (1H), 8.55 (2H), 8.71 (1H), 8.79 (1H), 10.26 (1H).

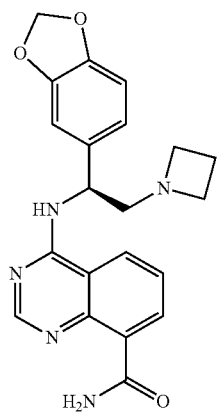 [SMILES: NC(=O)c1cccc2c(N[C@H](CN3CCC3)c3ccc4c(c3)OCO4)ncnc12]

4-[(S)-2-Azetidin-1-yl-1-(1-benzo[1,3]dioxol)-ethylamino]-quinazoline-8-carboxylic acid amide (20)

IC$_{50}$ p70S6K [nM]: 1.7
pS6 MDA-MB-468 [nM]: 68
Akt1 IC$_{50}$ [nM]: 120
Aurora B IC$_{50}$ [nM]: 300

Example 20 was prepared following the general synthesis of A-E starting with (S)-2-Amino-2-benzo[1,3]dioxol-5-yl-ethanol. LCMS [392.20 (M+1)]. $^1$H NMR (DMSO-d$_6$, ppm) 1.92 (2H), 2.68 (1H), 2.97 (1H), 3.13 (4H), 5.38 (1H), 5.95 (2H), 6.84 (1H), 6.90 (1H), 7.06 (1H), 7.66 (1H), 7.84 (1H), 8.54 (m, 4H), 10.35 (1H).

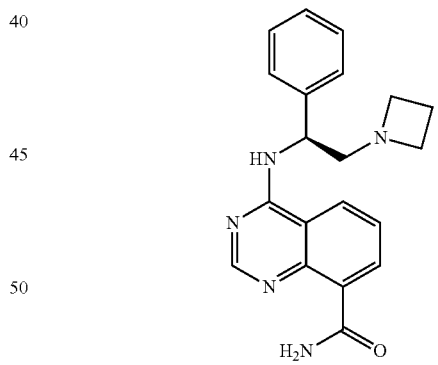

4-[(S)-2-Azetidin-1-yl-1-phenyl-ethylamino]-quinazoline-8-carboxylic acid amide (21)

IC$_{50}$ p70S6K [nM]: 11
pS6 MDA-MB-468 [nM]: 3100

Example 21 was prepared following the general synthesis of A-E starting with (S)-2-Amino-2-phenyl-ethanol. LCMS [348.20 (M+1)].

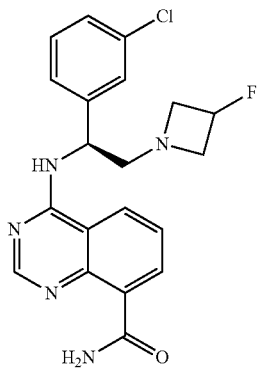 [SMILES: NC(=O)c1cccc2c(N[C@H](CN3CC(F)C3)c3cccc(Cl)c3)ncnc12]

4-[(S)-2-(3-Fluoro-azetidin-1-yl)-1-(3-chlorophe-nyl)-ethylamino]-quinazoline-8-carboxylic acid amide (22)

$IC_{50}$ p70S6K [nM]: 2.4
pS6 MDA-MB-468 [nM]: 324
Akt1 $IC_{50}$ [nM]: 72

Example 22 was prepared following the general synthesis of A-E starting with (S)-2-Amino-2-(3-chloro-phenyl)-ethanol and 3-F-azetidine. LCMS [399.9 (M+1)].

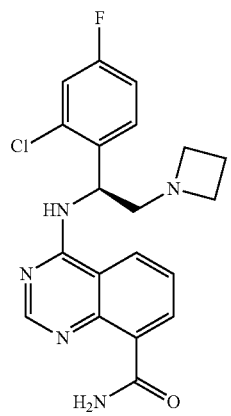

4-[(S)-2-Azetidin-1-yl-1-(2-chloro-4-fluoro-phenyl)-ethylamino]-quinazoline-8-carboxylic acid amide (24)

$IC_{50}$ p70S6K [nM]: 8.7
pS6 MDA-MB-468 [nM]: 1030
Akt1 $IC_{50}$ [nM]: 77
Aurora B $IC_{50}$ [nM]: 107

Example 24 was prepared following the general synthesis of A-E starting with (S)-2-amino-2-(2-chloro-4-fluoro-phenyl)-ethanol. LCMS [400.10 (M+1)].

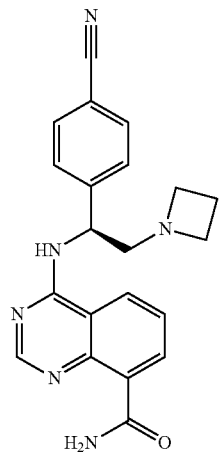 [SMILES: N#Cc1ccc([C@@H](CN2CCC2)Nc2ncnc3c(C(N)=O)cccc23)cc1]

4-[(S)-2-Azetidin-1-yl-1-(4-cyano-phenyl)-ethylamino]-quinazoline-8-carboxylic acid amide (23)

$IC_{50}$ p70S6K [nM]: 1.3
pS6 MDA-MB-468 [nM]: 29
Akt1 $IC_{50}$ [nM]: 11
Aurora B $IC_{50}$ [nM]: 150

Example 23 was prepared following the general synthesis of A-E starting with 4-((S)-1-amino-2-hydroxy-ethyl)-benzonitrile. LCMS [373.20 (M+1)].

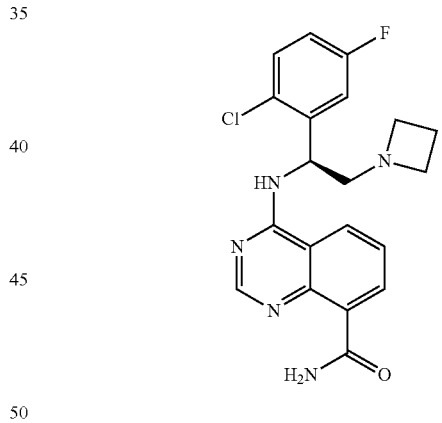

4-[(S)-2-Azetidin-1-yl-1-(2-chloro-5-fluoro-phenyl)-ethylamino]-quinazoline-8-carboxylic acid amide (25)

$IC_{50}$ p70S6K [nM]: 3.1
pS6 MDA-MB-468 [nM]: 486.0
Akt1 $IC_{50}$ [nM]: 370
Aurora B $IC_{50}$ [nM]: 259

Example 25 was prepared following the general synthesis of A-E starting with (S)-2-amino-2-(2-chloro-5-fluoro-phenyl)-ethanol. LCMS [400.10 (M+1)].

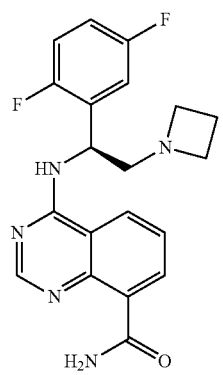 [SMILES: NC(=O)c1cccc2c(N[C@H](CN3CCC3)c3cc(F)ccc3F)ncnc12]

4-[(S)-2-Azetidin-1-yl-1-(2,5-di-fluoro-phenyl)-ethylamino]-quinazoline-8-carboxylic acid amide (26)

IC$_{50}$ p70S6K [nM]: 5.3
pS6 MDA-MB-468 [nM]: 359
Akt1 IC$_{50}$ [nM]: 98
Aurora B IC$_{50}$ [nM]: 230

Example 26 was prepared following the general synthesis of A-E starting with (S)-2-amino-2-(2,5-di-fluoro-phenyl)-ethanol. LCMS [384.10 (M+1)].

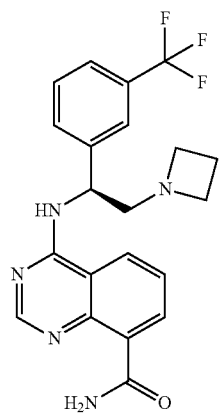 [SMILES: NC(=O)c1cccc2c(N[C@H](CN3CCC3)c3cccc(C(F)(F)F)c3)ncnc12]

4-[(S)-2-Azetidin-1-yl-1-(3-trifluoromethyl-phenyl)-ethylamino]-quinazoline-8-carboxylic acid amide (27)

IC$_{50}$ p70S6K [nM]: 1.4
pS6 MDA-MB-468 [nM]: 56.0
Akt1 IC$_{50}$ [nM]: 5.6
Aurora B IC$_{50}$ [nM]: 180

Example 27 was prepared following the general synthesis of A-E starting with (S)-2-amino-2-(3-trifluoro-phenyl)-ethanol. LCMS [416.10 (M+1)]. $^1$H NMR (500 MHz, CD$_3$OD) δ 8.69 (dd, J=7.5, 1.4, 1H), 8.61 (s, 1H), 8.48 (dd, J=8.3, 1.4, 1H), 7.84 (s, 1H), 7.78 (d, J=7.6, 1H), 7.73-7.65 (m, 3H), 7.65-7.55 (m, 2H), 5.92 (s, 1H), 3.90 (s, 4H), 3.52 (d, J=37.9, 2H), 2.40-2.26 (m, 2H).

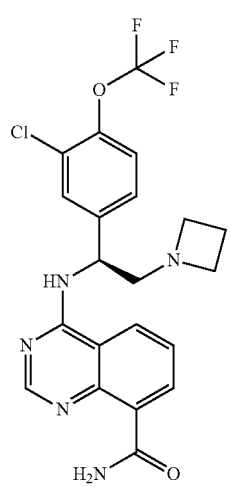 [SMILES: NC(=O)c1cccc2c(N[C@H](CN3CCC3)c3ccc(OC(F)(F)F)c(Cl)c3)ncnc12]

4-[(S)-2-Azetidin-1-yl-1-(3-chloro-4-trifluoromethoxy-phenyl)-ethylamino]-quinazoline-8-carboxylic acid amide (28)

IC$_{50}$ p70S6K [nM]: 2.4
pS6 MDA-MB-468 [nM]: 61.0
Aurora B IC$_{50}$ [nM]: 690

Example 28 was prepared following the general synthesis of A-E starting with (S)-2-amino-2-(3-chloro-4-trifluoromethoxy-phenyl)-ethanol. LCMS [466.10 (M+1)].

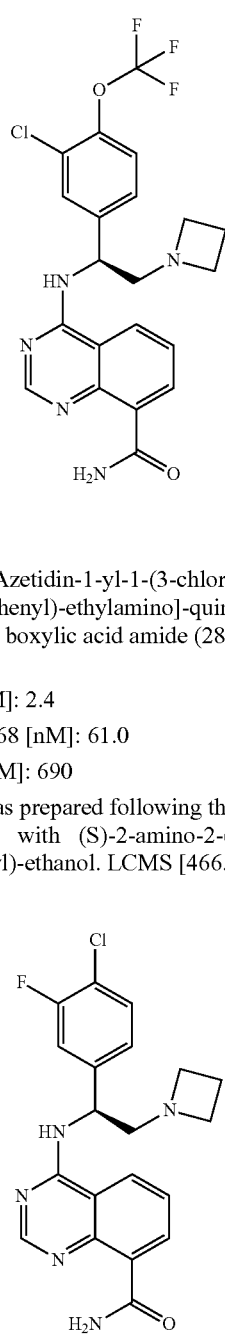

4-[(S)-2-Azetidin-1-yl-1-(4-chloro-3-fluoro-phenyl)-ethylamino]-quinazoline-8-carboxylic acid amide (29)

IC$_{50}$ p70S6K [nM]: 1.6
pS6 MDA-MB-468 [nM]: 19.0
Akt1 IC$_{50}$ [nM]: 7.7
Aurora B IC$_{50}$ [nM]: 75

Example 29 was prepared following the general synthesis of A-E starting with (S)-2-amino-2-(3-chloro-4-fluoro-phenyl)-ethanol. LCMS [466.10 (M+1)].

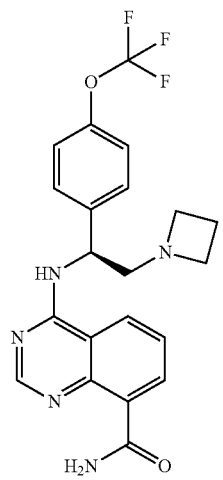 [SMILES: NC(=O)c1cccc2c(N[C@H](CN3CCC3)c3ccc(OC(F)(F)F)cc3)ncnc12]

4-[(S)-2-Azetidin-1-yl-1-(4-trifluoromethoxy-phenyl)-ethylamino]-quinazoline-8-carboxylic acid amide (30)

IC$_{50}$ p70S6K [nM]: 1.7
pS6 MDA-MB-468 [nM]: 199
Akt1 IC$_{50}$ [nM]: 187
Aurora B IC$_{50}$ [nM]: 370

Example 30 was prepared following the general synthesis of A-E starting with (S)-2-amino-2-(4-trifluoromethoxy-phenyl)-ethanol. LCMS [432.10 (M+1)].

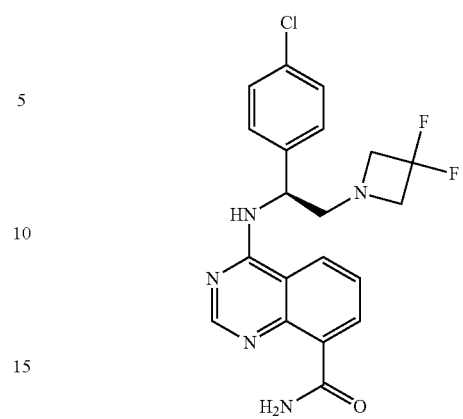

4-[(S)-1-(4-Chloro-phenyl)-2-(3,3-difluoro-azetidin-1-yl)-ethylamino]-quinazoline-8-carboxylic acid amide (32)

IC$_{50}$ p70S6K [nM]: 42
pS6 MDA-MB-468 [nM]: >10
Aurora B IC$_{50}$ [nM]: 340

Example 32 was prepared following the general synthesis of A-E starting with (S)-2-amino-2-(4-chloro-phenyl)-ethanol and 3,3'-di-fluoro azetidine. LCMS [418.10 (M+1)]. $^1$H NMR (DMSO-d$_6$, ppm) 3.10-3.50 (6H), 5.50 (1H), 7.40 (2H), 7.7 (1H), 7.80 (1H), 8.75 (5H), 10.20 (1H).

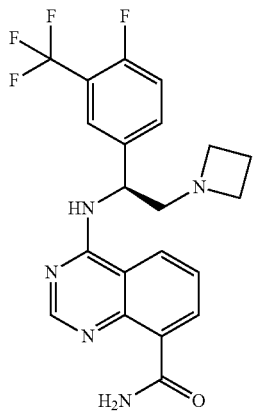 [SMILES: NC(=O)c1cccc2c(N[C@H](CN3CCC3)c3ccc(F)c(C(F)(F)F)c3)ncnc12]

4-[(S)-2-Azetidin-1-yl-1-(4-fluoro-3-trifluoromethyl-phenyl)-ethylamino]-quinazoline-8-carboxylic acid amide (31)

IC$_{50}$ p70S6K [nM]: 2.4
pS6 MDA-MB-468 [nM]: 28
Akt1 IC$_{50}$ [nM]: 7.3
Aurora B IC$_{50}$ [nM]: 285

Example 31 was prepared following the general synthesis of A-E starting with (S)-2-amino-2-(4-fluoro-3-trifluoromethyl-phenyl)-ethanol. LCMS [434.20 (M+1)]. $^1$H NMR (DMSO-d$_6$, ppm) 2.33 (2H), 3.78 (2H), 4.02 (3H), 4.42 (1H), 5.93 (1H), 7.54 (1H), 7.56 (1H), 7.72 (1H), 7.86 (1H), 8.57 (3H), 9.07 (1H), 10.14 (2H).

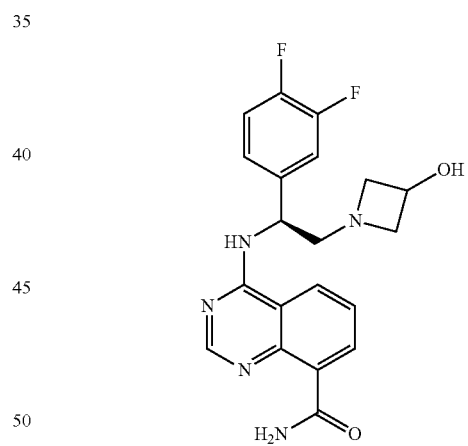

4-[(S)-1-(3,4-Difluoro-phenyl)-2-(3-hydroxy-azetidin-1-yl)-ethylamino]-quinazoline-8-carboxylic acid amide (33)

IC$_{50}$ p70S6K [nM]: 4.6
Aurora B IC$_{50}$ [nM]: 210

Example 33 was prepared following the general synthesis of A-E starting with (S)-2-amino-2-(3,4-di-fluoro-phenyl)-ethanol and 3-hydroxy azetidine. LCMS [400.20 (M+1)]. $^1$H NMR (MeOH-d$_4$, ppm) 2.90 (3H), 3.18 (1H), 3.60 (2H), 4.30 (1H), 5.50 (1H), 7.20 (2H), 7.35 (1H), 7.65 (1H), 8.5 (2H), 8.65 (1H).

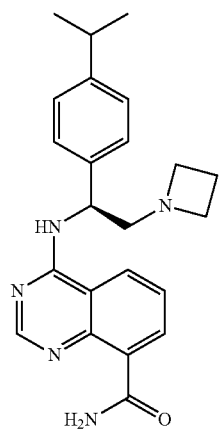 [SMILES: CC(C)c1ccc([C@@H](CN2CCC2)Nc2ncnc3c(C(N)=O)cccc23)cc1]

4-[(S)-2-Azetidin-1-yl-1-(4-isopropylphenyl)-ethylamino]-quinazoline-8-carboxylic acid amide (34)

IC$_{50}$ p70S6K [nM]: 0.8 pS6 MDA-MB-468 [nM]: 63

Example 34 was prepared following the general synthesis of A-E starting with (S)-2-amino-2-(4-isopropyl-phenyl)-ethanol. LCMS [390.20 (M+1)]. $^1$H NMR (DMSO-d$_6$, ppm) 1.16 (6H), 1.90 (2H), 2.69 (1H), 2.81 (1H), 2.86 (1H), 3.14 (4H), 5.42 (1H), 7.18 (2H), 7.35 (2H), 7.66 (1H), 7.82 (1H), 8.52 (1H), 8.56 (1H), 8.67 (2H), 10.35 (1H).

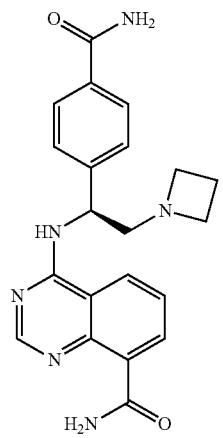 [SMILES: NC(=O)c1ccc([C@@H](CN2CCC2)Nc2ncnc3c(C(N)=O)cccc23)cc1]

4-[(S)-2-Azetidin-1-yl-1-(4-carbamoylphenyl)-ethylamino]-quinazoline-8-carboxylic acid amide (35)

IC$_{50}$ p70S6K [nM]: 8.6 pS6 MDA-MB-468 [nM]: 577

Example 35 was prepared following the general synthesis of A-E starting with (S)-2-amino-2-(4-carbamoylphenyl)-ethanol. LCMS [391.20 (M+1)].

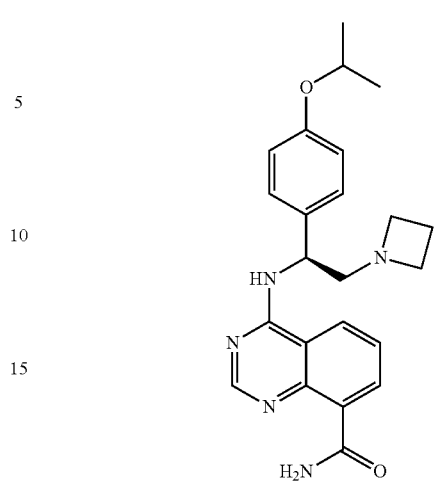

4-[(S)-2-Azetidin-1-yl-1-(4-isopropoxyphenyl)-ethylamino]-quinazoline-8-carboxylic acid amide (36)

IC$_{50}$ p70S6K [nM]: 400 pS6 MDA-MB-468 [uM]: >10

Example 36 was prepared following the general synthesis of A-E starting with (S)-2-amino-2-(4-isopropoxy-phenyl)-ethanol. LCMS [406.20 (M+1)].

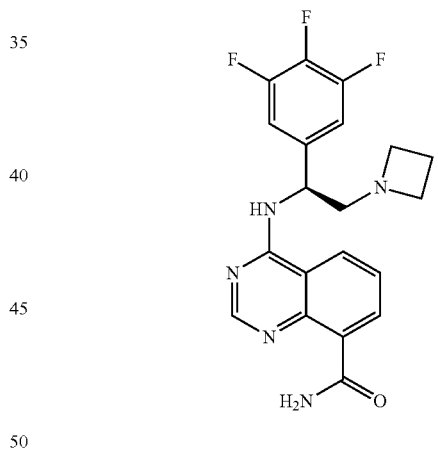

4-[(S)-2-Azetidin-1-yl-1-(3,4,5-trifluorophenyl)-ethylamino]-quinazoline-8-carboxylic acid amide (37)

IC$_{50}$ p70S6K [nM]: 2.8 pS6 MDA-MB-468 [nM]: 130

Akt1 IC$_{50}$ [nM]: 25

Aurora B IC$_{50}$ [nM]: 200

Example 37 was prepared following the general synthesis of A-E starting with (S)-2-amino-2-(3,4,5-trifluorophenyl)-ethanol. LCMS [402.20 (M+1)].

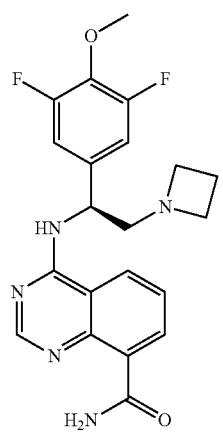 [SMILES: COc1c(F)cc([C@@H](CN2CCC2)Nc2ncnc3c(C(N)=O)cccc23)cc1F]

4-[(S)-2-Azetidin-1-yl-1-(3,5-difluoro-4-methoxyphenyl)-ethylamino]-quinazoline-8-carboxylic acid amide (38)

IC$_{50}$ p70S6K [nM]: 1.8
pS6 MDA-MB-468 [nM]: 113
Akt1 IC$_{50}$ [nM]: 140
Aurora B IC$_{50}$ [nM]: 280

Example 38 was prepared following the general synthesis of A-E starting with (S)-2-amino-2-(3,5-difluoro-4-methoxyphenyl)-ethanol. LCMS [414.20 (M+1)].

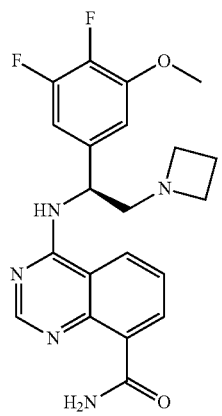

4-[(S)-2-Azetidin-1-yl-1-(3,4-difluoro-5-methoxyphenyl)-ethylamino]-quinazoline-8-carboxylic acid amide (40)

IC$_{50}$ p70S6K [nM]: 130
pS6 MDA-MB-468 [uM]: >10
Akt1 IC$_{50}$ [nM]: >1
Aurora B IC$_{50}$ [nM]: >1

Example 40 was prepared following the general synthesis of A-E starting with (S)-2-amino-2-(3,4-difluoro-5-methoxyphenyl)-ethanol. LCMS [414.25 (M+1)].

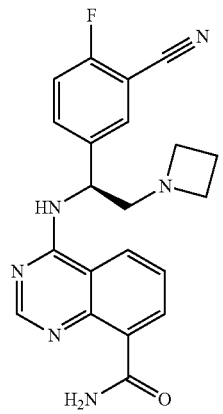 [SMILES: N#Cc1cc([C@@H](CN2CCC2)Nc2ncnc3c(C(N)=O)cccc23)ccc1F]

4-[(S)-2-Azetidin-1-yl-1-(3-cyano-4-fluorophenyl)-ethylamino]-quinazoline-8-carboxylic acid amide (39)

IC$_{50}$ p70S6K [nM]: 3.3
pS6 MDA-MB-468 [nM]: 246
Akt1 IC$_{50}$ [nM]: 83
Aurora B IC$_{50}$ [nM]: 650

Example 39 was prepared following the general synthesis of A-E starting with (S)-2-amino-2-(3-cyano-4-fluorophenyl)-ethanol. LCMS [391.20 (M+1)].

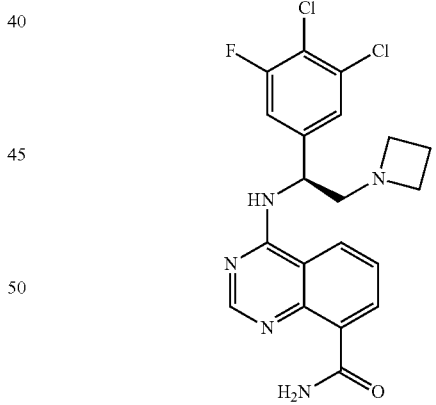

4-[(S)-2-Azetidin-1-yl-1-(3-fluoro-4,5-dichlorophenyl)-ethylamino]-quinazoline-8-carboxylic acid amide (41)

Example 41 was prepared following the general synthesis of A-E starting with (S)-2-amino-2-(3-fluoro-4,5-dichlorophenyl)-ethanol. LCMS [434.20 (M+1)].

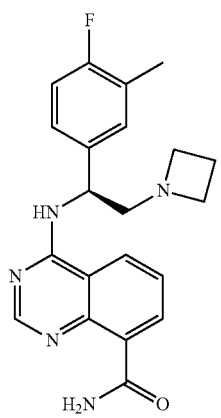

4-[(S)-2-Azetidin-1-yl-1-(4-fluoro-3-methyl-phenyl)-ethylamino]-quinazoline-8-carboxylic acid amide (42)

IC$_{50}$ p70S6K [nM]: 1.6
pS6 MDA-MB-468 [nM]: 32
Akt1 IC$_{50}$ [nM]: 23
Aurora B IC$_{50}$ [nM]: 120

Example 42 was prepared following the general synthesis of A-E starting with (S)-2-amino-2-(4-fluoro-3-methylphenyl)ethanol. LCMS [380.2 (M+1)]. $^1$H NMR (400 MHz, DMSO) δ 10.33 (d, J=3.8 Hz, 1H), 8.65 (dd, J=11.3, 4.4 Hz, 2H), 8.59 (dd, J=7.5, 1.3 Hz, 1H), 8.53 (s, 1H), 7.80 (d, J=3.9 Hz, 1H), 7.67 (t, J=7.9 Hz, 1H), 7.42-7.24 (m, 2H), 7.13-7.00 (m, 1H), 5.42 (dd, J=13.8, 8.8 Hz, 1H), 3.15 (t, J=6.9 Hz, 4H), 2.99 (dd, J=11.8, 9.3 Hz, 1H), 2.71 (dd, J=11.9, 5.4 Hz, 1H), 2.22 (d, J=1.2 Hz, 3H), 1.92 (p, J=6.9 Hz, 2H).

DMSO) δ 10.32 (d, J=2.9 Hz, 1H), 8.70-8.50 (m, 4H), 7.78 (s, 1H), 7.67 (t, J=7.8 Hz, 1H), 7.30 (d, J=8.3 Hz, 1H), 7.12 (dd, J=11.3, 8.4 Hz, 1H), 7.01 (d, J=4.2 Hz, 1H), 5.45 (dd, J=13.9, 8.5 Hz, 1H), 3.84 (s, 3H), 3.15 (t, J=6.9 Hz, 4H), 3.05-2.93 (m, 1H), 2.72 (dd, J=11.9, 5.2 Hz, 1H), 1.91 (p, J=6.9 Hz, 2H).

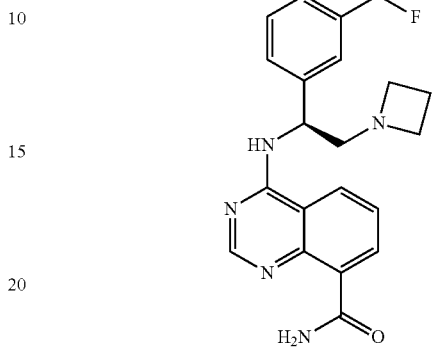

4-[(S)-2-Azetidin-1-yl-1-(3-difluoromethyl-4-fluoro-phenyl)-ethylamino]-quinazoline-8-carboxylic acid amide (44)

IC$_{50}$ p70S6K [nM]: 1.7
pS6 MDA-MB-468 [nM]: 41
Akt1 IC$_{50}$ [nM]: 7.3
Aurora B IC$_{50}$ [nM]: 75

Example 44 was prepared following the general synthesis of A-E starting with (S)-2-amino-2-(3-(difluoromethyl)-4-fluorophenyl)ethanol. LCMS [416.2 (M+1)]. $^1$H NMR (400 MHz, DMSO) δ 10.28 (d, J=3.3 Hz, 1H), 8.74 (d, J=7.7 Hz, 1H), 8.70-8.49 (m, 2H), 7.89-7.64 (m, 3H), 7.34 (dd, J=11.1, 7.7 Hz, 1H), 7.20 (s, 1H), 7.06 (s, 1H), 5.52 (s, 1H), 3.60-2.72 (m, 9H), 1.97 (s, 2H).

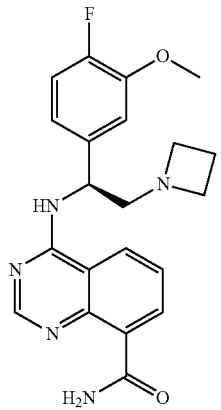 [SMILES: COc1cc([C@@H](CN2CCC2)Nc2ncnc3c(C(N)=O)cccc23)ccc1F]

4-[(S)-2-Azetidin-1-yl-1-(4-fluoro-3-methoxy-phenyl)-ethylamino]-quinazoline-8-carboxylic acid amide (43)

IC$_{50}$ p70S6K [nM]: 4
pS6 MDA-MB-468 [nM]: 484
Akt1 IC$_{50}$ [nM]: 21
Aurora B IC$_{50}$ [nM]: 69

Example 43 was prepared following the general synthesis of A-E starting with(S)-2-amino-2-(4-fluoro-3-methoxyphenyl)ethanol. LCMS [396.2 (M+1)]. $^1$H NMR (400 MHz,

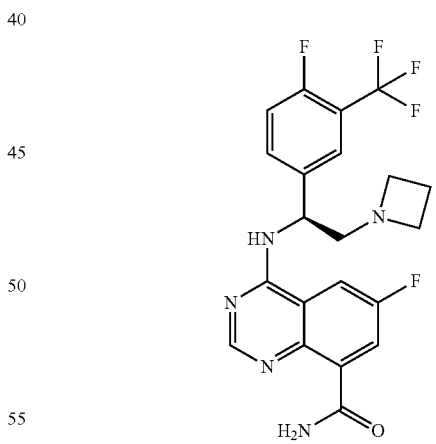

4-[(S)-2-Azetidin-1-yl-1-(4-fluoro-3-trifluoromethyl-phenyl)-ethylamino]-6-fluoro-quinazoline-8-carboxylic acid amide (45)

IC$_{50}$ p70S6K [nM]: 1.5
pS6 MDA-MB-468 [nM: 33
Akt1 IC$_{50}$ [nM]: 5.9
Aurora B IC$_{50}$ [nM]: 290

Example 45 was prepared following the general synthesis of A-E starting with (S)-2-amino-2-(4-fluoro-3-(trifluoromethyl)phenyl)ethanol and using the 6-fluoro derivative of D. LCMS [452.2 (M+1)]. $^1$H NMR (400 MHz, DMSO) δ 10.24 (d, J=3.3 Hz, 1H), 8.67 (d, J=7.5 Hz, 1H), 8.58-8.48 (m, 2H), 8.33 (dd, J=9.6, 2.9 Hz, 1H), 8.00 (d, J=3.3 Hz, 1H), 7.88 (d, J=6.7 Hz, 1H), 7.85-7.79 (m, 1H), 7.56-7.37 (m, 1H), 5.46 (d, J=6.8 Hz, 1H), 3.17 (dd, J=14.9, 7.1 Hz, 4H), 3.06-2.90 (m, 1H), 2.79 (dd, J=11.7, 5.9 Hz, 1H), 1.92 (p, J=6.9 Hz, 2H).

4-[(S)-2-Azetidin-1-yl-1-(4-fluoro-3-trifluoromethyl-phenyl)-ethylamino]-6-methoxy-quinazoline-8-carboxylic acid amide (47)

IC$_{50}$ p70S6K [nM]: 2.2 pS6 MDA-MB-468 [nM]: 27

Akt1 IC$_{50}$ [nM]: 1.5

Aurora B IC$_{50}$ [nM]: 200

Example 47 was prepared following the general synthesis of A-E starting with (S)-2-amino-2-(4-fluoro-3-(trifluoromethyl)phenyl)ethanol and using the 6-methoxy derivative of D. LCMS [464.2 (M+1)]. $^1$H NMR (400 MHz, DMSO) δ 10.34 (d, J=3.8 Hz, 1H), 8.56 (d, J=7.8 Hz, 1H), 8.44 (s, 1H), 8.18 (d, J=2.9 Hz, 1H), 8.03 (d, J=2.9 Hz, 1H), 7.94-7.77 (m, 3H), 7.54-7.41 (m, 1H), 5.51 (dd, J=14.4, 8.0 Hz, 1H), 3.98 (s, 3H), 3.20 (dq, J=17.2, 6.8 Hz, 5H), 3.02 (dd, J=11.9, 8.8 Hz, 1H), 2.84 (dd, J=11.9, 6.1 Hz, 1H), 1.94 (p, J=6.9 Hz, 2H).

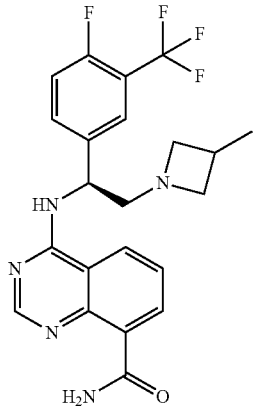 [SMILES: CC1CN(C[C@@H](Nc2ncnc3c(C(N)=O)cccc23)c2ccc(F)c(C(F)(F)F)c2)C1]

4-[(S)-1-(4-Fluoro-3-trifluoromethyl-phenyl)-2-(3-methyl-azetidin-1-yl)-ethylamino]-quinazoline-8-carboxylic acid amide (46)

IC$_{50}$ p70S6K [nM]: 4.9 pS6 MDA-MB-468 [nM]: 427

Akt1 IC$_{50}$ [nM]: 7.5

Aurora B IC$_{50}$ [nM]: 390

Example 46 was prepared following the general synthesis of A-E starting with (S)-2-amino-2-(4-fluoro-3-(trifluoromethyl)phenyl)ethanol and using 3-methylazetidine. LCMS [448.2 (M+1)]. $^1$H NMR (400 MHz, DMSO) δ 10.26 (s, 1H), 8.73 (d, J=7.7 Hz, 1H), 8.61 (dd, J=15.9, 7.8 Hz, 2H), 8.54 (s, 1H), 7.94-7.86 (m, 1H), 7.86-7.75 (m, 2H), 7.69 (t, J=7.8 Hz, 1H), 7.51-7.40 (m, 1H), 5.49 (dd, J=14.1, 8.0 Hz, 1H), 3.48-3.35 (m, 2H), 3.07-2.94 (m, 1H), 2.87-2.70 (m, 2H), 2.39 (tt, J=16.8, 8.5 Hz, 1H), 1.05 (d, J=6.7 Hz, 3H).

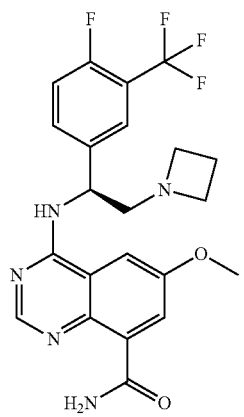 [SMILES: COc1cc(C(N)=O)c2ncnc(N[C@H](CN3CCC3)c3ccc(F)c(C(F)(F)F)c3)c2c1]

4-[(S)-1-(4-Fluoro-3-trifluoromethyl-phenyl)-2-(2-methyl-azetidin-1-yl)-ethylamino]-quinazoline-8-carboxylic acid amide (48)

IC$_{50}$ p70S6K [nM]: 3 pS6 MDA-MB-468 [nM]: 391

Akt1 IC$_{50}$ [nM]: 11

Aurora B IC$_{50}$ [nM]: 120

Example 48 was prepared following the general synthesis of A-E starting with (S)-2-amino-2-(4-fluoro-3-(trifluoromethyl)phenyl)ethanol and using 2-methylazetidine. LCMS [448.2 (M+1)]. $^1$H NMR (400 MHz, DMSO) δ 10.26 (s, 1H), 8.72 (dd, J=29.4, 7.8 Hz, 1H), 8.60 (ddd, J=8.7, 7.9, 1.7 Hz, 2H), 8.55 (s, 1H), 7.93 (t, J=5.7 Hz, 1H), 7.89-7.75 (m, 2H), 7.74-7.65 (m, 1H), 7.53-7.40 (m, 1H), 5.52 (d, J=5.2 Hz, 1H), 3.25-3.06 (m, 2H), 3.03-2.61 (m, 3H), 2.08-1.91 (m, 1H), 1.62 (dd, J=15.8, 8.6 Hz, 1H), 1.07 (dd, J=47.8, 6.0 Hz, 3H).

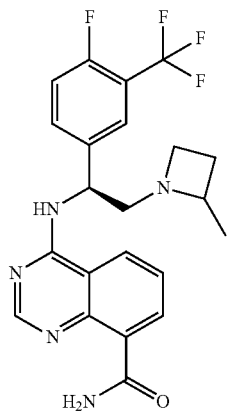 [SMILES: CC1CCN1C[C@@H](Nc1ncnc2c(C(N)=O)cccc12)c1ccc(F)c(C(F)(F)F)c1]

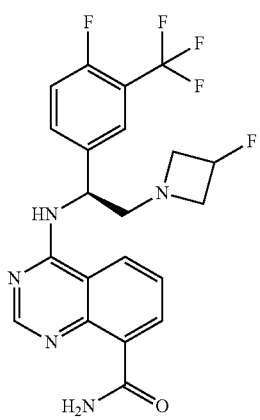

4-[(S)-2-(3-Fluoro-azetidin-1-yl)-1-(4-fluoro-3-trifluoromethyl-phenyl)-ethylamino]-quinazoline-8-carboxylic acid amide (49)

IC$_{50}$ p70S6K [nM]: 5
pS6 MDA-MB-468 [nM]: 116
Akt1 IC$_{50}$ [nM]: 16
Aurora B IC$_{50}$ [nM]: 540

Example 49 was prepared following the general synthesis of A-E starting with (S)-2-amino-2-(4-fluoro-3-(trifluoromethyl)phenyl)ethanol and using 3-fluoroazetidine. LCMS [452.2 (M+1)]. $^1$H NMR (400 MHz, DMSO) δ 10.26 (d, J=3.5 Hz, 1H), 8.76 (d, J=7.8 Hz, 1H), 8.68-8.50 (m, 3H), 7.97-7.89 (m, 1H), 7.86 (dd, J=8.2, 5.2 Hz, 1H), 7.80 (d, J=3.3 Hz, 1H), 7.69 (t, J=7.9 Hz, 1H), 7.55-7.41 (m, 1H), 5.54 (dd, J=14.0, 8.5 Hz, 1H), 5.24-4.99 (m, 1H), 3.58 (ddd, J=24.2, 15.2, 6.9 Hz, 2H), 3.25 (dd, J=8.6, 4.4 Hz, 1H), 3.23-3.16 (m, 1H), 3.11 (dd, J=11.9, 9.2 Hz, 1H), 2.90 (dd, J=11.9, 5.7 Hz, 1H).

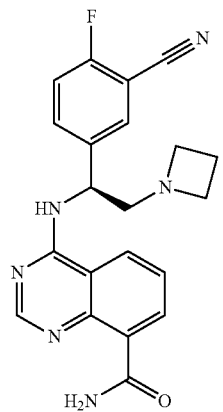 [SMILES: N#Cc1cc([C@@H](CN2CCC2)Nc2ncnc3c(C(N)=O)cccc23)ccc1F]

4-[(S)-2-Azetidin-1-yl-1-(3-cyano-4-fluoro-phenyl)-ethylamino]-quinazoline-8-carboxylic acid amide (50)

IC$_{50}$ p70S6K [nM]: 3.3
pS6 MDA-MB-468 [nM]: 246
Akt1 IC$_{50}$ [nM]: 83
Aurora B IC$_{50}$ [nM]: 650

Example 50 was prepared following the general synthesis of A-E starting with (S)-5-(1-amino-2-hydroxyethyl)-2-fluorobenzonitrile. LCMS [391.2 (M+1)]. $^1$H NMR (400 MHz, DMSO) δ 10.27 (d, J=3.7 Hz, 1H), 8.67 (d, J=7.8 Hz, 1H), 8.64-8.57 (m, 2H), 8.53 (d, J=10.3 Hz, 1H), 8.02 (dd, J=6.2, 2.2 Hz, 1H), 7.90-7.83 (m, 1H), 7.80 (d, J=3.7 Hz, 1H), 7.69 (t, J=7.9 Hz, 1H), 7.48 (td, J=9.0, 2.9 Hz, 1H), 5.51-5.35 (m, 1H), 3.25-3.08 (m, 4H), 2.95 (dt, J=16.3, 8.1 Hz, 1H), 2.78 (dd, J=11.9, 6.2 Hz, 1H), 1.92 (p, J=7.0 Hz, 2H).

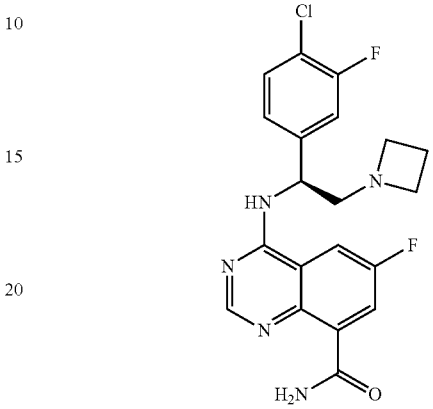

4-[(S)-2-Azetidin-1-yl-1-(4-chloro-3-fluoro-phenyl)-ethylamino]-6-fluoro-quinazoline-8-carboxylic acid amide (51)

IC$_{50}$ p70S6K [nM]: 1
pS6 MDA-MB-468 [nM]: 64
Aurora B IC$_{50}$ [nM]: 54

Example 51 was prepared following the general synthesis of A-E starting with (S)-2-amino-2-(4-chloro-3-fluorophenyl)ethanol and using the 6-fluoro derivative of compound D. LCMS [418.2 (M+1)]. $^1$H NMR (500 MHz, CD$_3$OD) δ 8.55 (s, 1H), 8.43 (dd, J=9.4, 2.8 Hz, 1H), 8.28 (dd, J=8.6, 2.8 Hz, 1H), 7.45 (t, J=7.9 Hz, 1H), 7.37 (dd, J=10.2, 1.9 Hz, 1H), 7.28 (d, J=8.4 Hz, 1H), 5.63 (dd, J=9.4, 4.4 Hz, 2H), 3.55 (s, 4H), 3.13 (s, 1H), 2.28-2.09 (m, 2H).

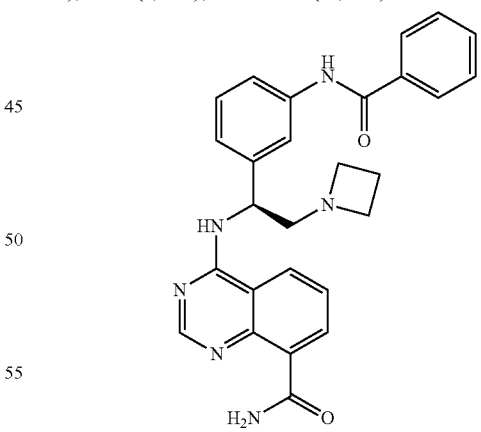

4-[(S)-2-Azetidin-1-yl-1-(4-benzoylamino-phenyl)-ethylamino]-quinazoline-8-carboxylic acid amide (52)

IC$_{50}$ p70S6K [nM]: 440
Aurora B IC$_{50}$ [nM]: >10

Example 52 was prepared following the general synthesis of A-E starting with (S)—N-(4-(1-amino-2-hydroxyethyl)

phenyl)benzamide. LCMS [467.2 (M+1)]. $^1$H NMR (500 MHz, cd$_3$od) δ 8.68 (d, J=7.5 Hz, 1H), 8.62 (s, 1H), 8.50 (d, J=8.3 Hz, 1H), 7.91 (d, J=7.8 Hz, 2H), 7.73 (d, J=8.5 Hz, 2H), 7.66 (t, J=7.9 Hz, 1H), 7.63-7.45 (m, 5H), 5.86 (s, 1H), 3.91 (s, 5H), 3.55 (d, J=48.2 Hz, 3H), 2.35 (s, 3H).

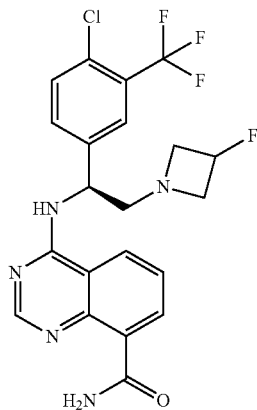 [SMILES: NC(=O)c1cccc2c(N[C@H](CN3CC(F)C3)c3ccc(Cl)c(C(F)(F)F)c3)ncnc12]

4-[(S)-2-(3-Fluoro-azetidin-1-yl)-1-(4-chloro-3-trifluoromethyl-phenyl)-ethylamino]-quinazoline-8-carboxylic acid amide (53)

Example 53 was prepared following the general synthesis of A-E starting with (S)-2-amino-2-(4-chloro-3-(trifluoromethyl)phenyl)ethanol and using 3-fluoroazetidine. LCMS [468.2 (M+1)].

Biological Activity p70S6K Enzyme Assay p70S6K inhibitor compounds were diluted and plated in 96 well plates. A reaction mixture including the following components were then added to the compound plate to initiate the enzyme reaction; P70S6K (3 nM, T412E mutant, Millipore) was mixed with 24 μM ATP in an assay buffer containing 100 mM Hepes (pH 7.5), 5 mM MgCl$_2$, 1 mM DTT, 0.015% Brij and 1 μM of the substrate peptide FITC-AHA-AKRRRLSS-LRA-OH (derived from the S6 ribosomal protein sequence, FITC=fluorescein isothiocyanate, AHA=6-aminohexanoic acid). The reaction was incubated for 90 min at 25° C., before the addition of 10 mM EDTA to stop the reaction. The proportion of substrate and product (phosphorylated) peptide was analysed on a Caliper Life Sciences Lab Chip 3000, using a pressure of −1.4 psi, and upstream and downstream voltages of −3000 and −700 respectively. Product peaks were resolved before substrate peaks on the resulting chromatograms.

To assess the inhibitory potential of the compounds, IC50-values were determined, as shown in Chemical Synthesis section above.

Cellular Activity Assay

MDA-MB-468 cells were grown in DMEM containing glutamine supplemented with 10% Fetal Bovine Serum (FBS) and 1× antibiotics. Cells were maintained by splitting 1:3 twice a week.

For the assay, cells were plated the evening before at a density of 4000 cells per well in black polyD lysine coated 384 well plates. Cells were incubated overnight (16 to 20 hours) in growth media. Compounds at an appropriate concentration were added to the wells and incubated for 2 hr.

Controls included: i) no primary, ii) rabbit isotype, iii) propidium iodide (red) only and iv) anti-phospho-S6 antibody alone (green only). Cells were then fixed in 4% paraformaldehyde for 15-20 minutes at room temperature, then washed 3×80 ul with PBS.

50 ul 10% normal goat serum (NGS) with 0.2% triton X 100 in PBS were added and incubated for 30 to 60 minutes at room temperature. Anti-phospho-S6 antibody was diluted 1:800 2% with NGS in 0.2% TritonX-100 and 30 ul added to appropriate wells. The wells were incubated overnight at 4 degrees Celsius.

Then the wells were washed with 3×80 uL PBS. The secondary green fluorescence labeled antibody (Alexa Fluor® 488 F(ab')2 fragment goat Anti-rabbit IgG (H+L)), was diluted 1:1500 in 2% NGS with 0.2% TritonX-100, and 30 ul were added to the appropriate wells which were then incubated in the dark at room temperature for 60 minutes. Then they were washed with 4×80 ul PBS. Propidium iodide (1.5 mM stock) was diluted 1:1000 in PBS, and 50 ul were added to the appropriate wells and incubated for 30 minutes at room temperature in the dark. Propidium iodide was not washed out. Plates were read on the Acumen Explorer.

Red and green cell populations were determined using controls. The number of green cells (pS6) and total number of cells (red) were then counted and the percentage of green cells was calculated. Percent positive cell data was plotted on a log scale against concentration of compounds and IC50 values were calculated from dose response curves.

Aurora B Kinase Assay

To measure inhibitor activity of Aurora B inhibitors in the Caliper Life Sciences LC3000, a TTP Mosquito liquid handling instrument was used to place 0.25 ul of the appropriate concentration of inhibitor in 100% DMSO (for a dose response curve calculation) into each well of a 384-well plate. To this reaction components was added to a final volume of 25 ul:

0.1 ng/ul GST-Aurora B (1-344 amino acids), (Carna Biosciences 05-102. N-terminal GST fusion with His tagged INCEP, accession number Q96GD4).

10 uM ATP (Fluka, 02055)

1 mM DTT (Sigma, D0632)

1 mM MgCl$_2$ (Sigma, M1028)

1 uM substrate peptide (sequence FITC-LRRASLG-(CONH2), synthesized by Tufts Peptide Synthesis service.

100 mM HEPES pH 7.5 (Calbiochem, 391338)

0.015% Brij-35 (Sigma, B4184)

The reaction was incubated for 90 min at 25 C, and then stopped by the addition of 70 ul of Stop buffer (100 mM HEPES pH 7.5, 0.015% Brij-35, 10 mM EDTA (Sigma, E7889)).

The plate was read on a Caliper LC 3000 in an Off-Chip mobility shift assay format, using the following parameters for a 12-sipper chip: screening pressure −1.8 psi, upstream voltage −2700, downstream voltage −1000. These conditions caused unphosphorylated substrate and phosphorylated product peptide to resolve as separate peaks allowing direct measurement of percentage of conversion of substrate to product. The percent conversion was plotted against concentration of inhibitor to produce a sigmoidal dose response curve, from which an IC50 was calculated using XLFit for Microsoft Excel.

AKT/PKB Kinase Assay

In order to measure AKT inhibition in the Caliper Life Sciences LC3000, a TTP Mosquito liquid handling instrument was used to place 125 nl of the appropriate concentration of inhibitor in 100% DMSO (for a dose response curve calculation) into each well of a 384-well plate. To this reaction components were added to a final volume of 12.5 ul:
- 0.1 ng/ul His-AKT (Full Length), (Invitrogen, Part #P2999, Lot #641228C)
- 160 uM ATP (Fluke, 02055)
- 1 mM DTT (Sigma, D0632)
- 1 mM $MgCl_2$ (Sigma, M1028)
- 1 uM substrate peptide (sequence FITC-AHA-GRPRTSS-FAEG-$NH_2$), synthesized by Tufts Peptide Synthesis service.
- 100 mM HEPES pH 7.5 (Calbiochem, 391338)
- 0.015% Brij-35 (Sigma, B4184)

The reaction was incubated for 90 min at 25 C, and then stopped by the addition of 70 ul of Stop buffer (100 mM HEPES pH 7.5, 0.015% Brij-35, 10 mM EDTA (Sigma, E7889)).

The plate was read on a Caliper LC 3000 in an Off-Chip mobility shift assay format, using the following parameters for a 12-sipper chip: screening pressure −2.3 psi, upstream voltage −500, and downstream voltage −3000.

These conditions cause unphosphorylated substrate and phosphorylated product peptide to resolve as separate peaks allowing direct measurement of percentage of conversion of substrate to product. The percent conversion was plotted against concentration of inhibitor to produce a sigmoidal dose response curve, from which an IC50 was calculated.

The invention claimed is:

1. A compound of Formula (II')

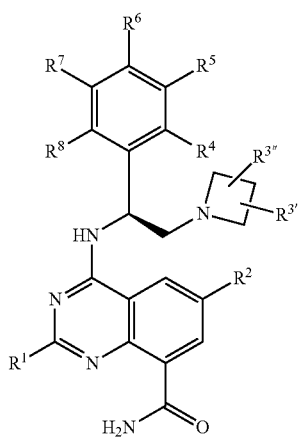

(II')

and/or its stereoisomers or tautomers, or pharmaceutically acceptable salts of each of the foregoing, including mixtures thereof in all ratios, wherein:

$R^1$, $R^2$ are H,
$R^{3'}$, $R^{3''}$ independently are H, LA or Hal,
$R^4$, $R^5$, $R^6$, $R^7$, $R^8$, independently are H, Hal, LA, OH, SH, O(LA), $NH_2$, NH(LA), $N(LA)_2$, $NO_2$, CN, OCN, SCN, COOH, COO(LA), $CONH_2$, CONH(LA), $CON(LA)_2$, NHCO(LA), NHCONH(LA), $NHCONH_2$, $NHSO_2$(LA), CO(LA), $SO_2NH_2$, $SO_2$(LA) or $SO_2$Hal, or $R^5$, $R^6$ together with the phenyl group they are attached to, may form a 9 or 10 membered bicyclic ring system, in which 1 or 2 of the non-phenyl carbon atoms may be independently replaced by NH, O or S, in which the cycle formed by $R^5$ and $R^6$ may be unsubstituted or mono- or disubstituted by Hal or LA, or one of $R^5$, $R^6$, $R^7$
may be Ar1, O(Ar1), NH(Ar1), CONH(Ar1), NHCO(Ar1), NHCONH(Ar1), $NHSO_2$(Ar1), CO(Ar1) or $SO_2$(Ar1),
while the other two of $R^5$, $R^6$, $R^7$ are not Ar1, O(Ar1), NH(Ar1), CONH(Ar1), NHCO(Ar1), NHCONH(Ar1), $NHSO_2$(Ar1), CO(Ar1) or $SO_2$(Ar1), Ar1 is a monocyclic aromatic homo- or heterocycle having 0, 1, 2 or 3 N, O and/or S atoms and 5 or 6 skeleton atoms, which may be unsubstituted or, independently of one another, mono-, di- or trisubstituted by Hal, LA, OH, SH, O(LA), $NH_2$, NH(LA), N(LA), $NO_2$, CN, OCN, SCN, COOH, COO(LA), $CONH_2$, CONH(LA), $CON(LA)_2$, NHCO(LA), CHO, CO(LA), $SO_2NH_2$, $SO_2$(LA) and/or $SO_2$Hal, LA is unbranched or branched, linear alkyl having 1, 2, 3 or 4 C atoms, wherein 1, 2 or 3 H atoms may be replaced by Hal, Hal is F, Cl or Br.

2. The compound according to claim 1, in which
$R^4$, $R^5$, $R^6$, $R^7$, $R^8$ independently are H, F, Cl, Br, OH, LA, O(LA), CN, C(Hal)$_3$, OC(Hal)$_3$, or $R^{3'}$, $R^{3''}$ independently are H or F, or $R^4$, $R^8$ independently are H, F or Cl, or $R^5$, $R^7$ independently are H, F, Cl, Br, CN, methoxy or $CF_3$, or $R^5$, $R^6$ together with the phenyl group they are attached to, form benzo-1,2-dioxolyl, of which the carbon atom bridging the two oxygen atoms may be unsubstituted, or mono- or disubstituted by F or methyl, or $R^6$ is H, F, Cl or $CF_3$, or $R^5$, $R^6$ independently are H, F, Cl, Br, methyl, $CHF_2$ or $CF_3$, or $R^1$, $R^2$, $R^{3'}$, $R^{3''}$, $R^4$, $R^7$, $R^8$ are H, or $R^1$, $R^2$, $R^{3'}$, $R^{3''}$, $R^4$, $R^7$, $R^8$ are H,
$R^5$, $R^6$ are independently H, F, Cl, Br, methyl, $CHF_2$ or $CF_3$, or $R^1$, $R^2$, $R^{3'}$, $R^{3''}$, $R^4$, $R^8$ are H,
$R^5$ is Br, methyl, $CHF_2$ or $CF_3$,
$R^6$ is F, Cl or $CF_3$,
$R^7$ is H or F, or $R^1$, $R^2$, $R^4$, $R^8$ are H,
$R^{3'}$ is F, or methyl,
$R^{3''}$ is H,
$R^5$ is Br, methyl, $CHF_2$ or $CF_3$,
$R^6$ is F, Cl or $CF_3$,
$R^7$ is H or F.

3. The compound according to claim 1, wherein the compound is:
- 4-[(S)-2-Azetidin-1-yl-(3-fluorophenyl)-ethylamino]-quinazoline-8-carboxylic acid amide;
- 4-[(S)-2-Azetidin-1-yl-1-(3-chlorophenyl)-ethylamino]-quinazoline-8-carboxylic acid amide;
- 4-[(S)-2-Azetidin-1-yl-1-(4-fluorophenyl)-ethylamino]-quinazoline-8-carboxylic acid amide;
- 4-[(S)-2-Azetidin-1-yl-1-(4-difluorophenyl)-ethylamino]-quinazoline-8-carboxylic acid amide;
- 4-[(S)-2-Azetidin-1-yl-1-(4-chloro-3-trifluoromethylphenyl)-ethylamino]-quinazoline-8-carboxylic acid amide;

4-[(S)-2-Azetidin-1-yl-1-(3-fluoro-5-trifluoromethylphenyl)-ethylamino]-quinazoline-8-carboxylic acid amide;
4-[(S)-2-Azetidin-1-yl-1-(3-chloro-4-fluorophenyl)-ethylamino]-quinazoline-8-carboxylic acid amide;
4-[(S)-2-Azetidin-1-yl-1-(4-bromophenyl)-ethylamino]-quinazoline-8-carboxylic acid amide;
4-[(S)-2-Azetidin-1-yl-1-(4-trifluoromethylphenyl)-ethylamino]-quinazoline-8-carboxylic acid amide;
4-[(S)-2-Azetidin-1-yl-1-(4-chlorophenyl)-ethylamino]-quinazoline-8-carboxylic acid amide;
4-[(S)-2-Azetidin-1-yl-1-(3-cyanophenyl)-ethylamino]-quinazoline-8-carboxylic acid amide;
4-[(S)-2-Azetidin-1-yl-1-(3-methoxyphenyl)-ethylamino]-quinazoline-8-carboxylic acid amide;
4-[(S)-2-Azetidin-1-yl-1-(3-bromophenyl)-ethylamino]-quinazoline-8-carboxylic acid amide;
4-[(S)-2-Azetidin-1-yl-1-(2-fluoro-4-chlorophenyl)-ethylamino]-quinazoline-8-carboxylic acid amide;
4-[(S)-2-Azetidin-1-yl-1-(2,4-difluorophenyl)-ethylamino]-quinazoline-8-carboxylic acid amide;
4-[(S)-2-Azetidin-1-yl-1-(2,6-difluorophenyl)-ethylamino]-quinazoline-8-carboxylic acid amide;
4-[(S)-2-Azetidin-1-yl-1-(3-chloro-4-trifluoromethylphenyl)-ethylamino]-quinazoline-8-carboxylic acid amide;
4-[(S)-2-Azetidin-1-yl-1-(2,4,5-trifluorophenyl)-ethylamino]-quinazoline-8-carboxylic acid amide;
4-[(S)-2-Azetidin-1-yl-1-(2,3,4-trifluorophenyl)-ethylamino]-quinazoline-8-carboxylic acid amide;
4-[(S)-2-Azetidin-1-yl-1-(1-benzo[1,3]dioxol)-ethylamino]-quinazoline-8-carboxylic acid amide;
4-[(S)-2-Azetidin-1-yl-1-phenyl-ethylamino]-quinazoline-8-carboxylic acid amide;
4-[(S)-2-(3-Fluoro-azetidin-1-yl)-1-(3-chlorophenyl)-ethylamino]-quinazoline-8-carboxylic acid amide;
4-[(S)-2-Azetidin-1-yl-1-(4-cyano-phenyl)-ethylamino]-quinazoline-8-carboxylic acid amide;
4-[(S)-2-Azetidin-1-yl-1-(2-chloro-4-fluoro-phenyl)-ethylamino]-quinazoline-8-carboxylic acid amide;
4-[(S)-2-Azetidin-1-yl-1-(2-chloro-5-fluoro-phenyl)-ethylamino]-quinazoline-8-carboxylic acid amide;
4-[(S)-2-Azetidin-1-yl-1-(2,5-di-fluoro-phenyl)-ethylamino]-quinazoline-8-carboxylic acid amide;
4-[(S)-2-Azetidin-1-yl-1-(3-trifluoromethyl-phenyl)-ethylamino]-quinazoline-8-carboxylic acid amide;
4-[(S)-2-Azetidin-1-yl-1-(3-chloro-4-trifluoromethoxy-phenyl)-ethylamino]-quinazoline-8-carboxylic acid amide;
4-[(S)-2-Azetidin-1-yl-1-(4-chloro-3-fluoro-phenyl)-ethylamino]-quinazoline-8-carboxylic acid amide;
4-[(S)-2-Azetidin-1-yl-1-(4-trifluoromethoxy-phenyl)-ethylamino]-quinazoline-8-carboxylic acid amide;
4-[(S)-2-Azetidin-1-yl-1-(4-fluoro-3-trifluoromethyl-phenyl)-ethylamino]-quinazoline-8-carboxylic acid amide;
4-[(S)-1-(4-Chloro-phenyl)-2-(3,3-difluoro-azetidin-1-yl)-ethylamino]-quinazoline-8-carboxylic acid amide;
4-[(S)-2-Azetidin-1-yl-1-(4-isopropylphenyl)-ethylamino]-quinazoline-8-carboxylic acid amide;
4-[(S)-2-Azetidin-1-yl-1-(4-isopropylphenyl)-ethylamino]-quinazoline-8-carboxylic acid amide;
4-[(S)-2-Azetidin-1-yl-1-(3,4,5-trifluorophenyl)-ethylamino]-quinazoline-8-carboxylic acid amide;
4-[(S)-2-Azetidin-1-yl-1-(3,5-difluoro-4-methoxyphenyl)-ethylamino]-quinazoline-8-carboxylic acid amide;
4-[(S)-2-Azetidin-1-yl-1-(3-cyano-4-fluorophenyl)-ethylamino]-quinazoline-8-carboxylic acid amide;
4-[(S)-2-Azetidin-1-yl-1-(3,4-difluoro-5-methoxyphenyl)-ethylamino]-quinazoline-8-carboxylic acid amide;
4-[(S)-2-Azetidin-1-yl-1-(3-fluoro-4,5-dichlorophenyl)-ethylamino]-quinazoline-8-carboxylic acid amide;
4-[(S)-2-Azetidin-1-yl-1-(4-fluoro-3-methyl-phenyl)-ethylamino]-quinazoline-8-carboxylic acid amide;
4-[(S)-2-Azetidin-1-yl-1-(4-fluoro-3-methoxy-phenyl)-ethylamino]-quinazoline-8-carboxylic acid amide;
4-[(S)-2-Azetidin-1-yl-1-(3-difluoromethyl-4-fluoro-phenyl)-ethylamino]-quinazoline-8-carboxylic acid amide;
4-[(S)-2-Azetidin-1-yl-1-(4-fluoro-3-trifluoromethyl-phenyl)-ethylamino]-6-fluoro-quinazoline-8-carboxylic acid amide;
4-[(S)-1-(4-Fluoro-3-trifluoromethyl-phenyl)-2-(3-methyl-azetidin-1-yl)-ethylamino]-quinazoline-8-carboxylic acid amide;
4-[(S)-1-(4-Fluoro-3-trifluoromethyl-phenyl)-2-(2-methyl-azetidin-1-yl)-ethylamino]-quinazoline-8-carboxylic acid amide;
4-[(S)-2-(3-Fluoro-azetidin-1-yl)-1-(4-fluoro-3-trifluoromethyl-phenyl)-ethylamino]-quinazoline-8-carboxylic acid amide;
4-[(S)-2-Azetidin-1-yl-1-(3-cyano-4-fluoro-phenyl)-ethylamino]-quinazoline-8-carboxylic acid amide;
4-[(S)-2-Azetidin-1-yl-1-(4-chloro-3-fluoro-phenyl)-ethylamino]-6-fluoro-quinazoline-8-carboxylic acid amide;
4-[(S)-2-Azetidin-1-yl-1-(4-benzoylamino-phenyl)-ethylamino]-quinazoline-8-carboxylic acid amide; or
4-[(S)-2-(3-Fluoro-azetidin-1-yl)-1-(4-chloro-3-trifluoromethyl-phenyl)-ethylamino]-quinazoline-8-carboxylic acid amide.

4. A pharmaceutical composition comprising a compound according to claim 1 as active ingredient, together with a pharmaceutically acceptable carrier.

5. A medicament comprising a compound of claim 1, as active ingredient, together with a pharmaceutically acceptable carrier.

6. A method for treating a disease comprising administering to a subject in need thereof, an effective amount of a compound of claim 1, wherein said disease is cancer, inflammation, pancreatitis or kidney disease, pain, benign hyperplasia of the skin, restenosis, prostate, diseases related to vasculogenesis or angiogenesis, tumor angiogenesis, skin disease, diabetes, diabetic retinopathy, retinopathy of prematurity, age-related macular degeneration, hemangioma, glioma, melanoma or Kaposi's sarcoma.

7. The method of claim 6, wherein the disease is cancer.

8. The method of claim 6, wherein the skin disease is psoriasis, eczema or sclerodema.

9. A kit consisting of separate packs of
  a) an effective amount of a compound according to claim 1, and
  b) an effective amount of a further medicament active ingredient.

10. A process for the manufacture of a compound according to claim 1, wherein LG is a leaving group, and wherein a compound of Formula (V)

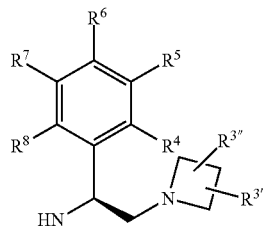

is reacted with a compound of Formula (IV)

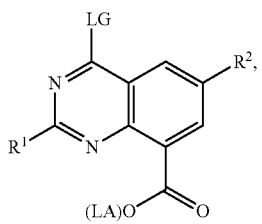

to yield a carboxylic ester compound of Formula (III),

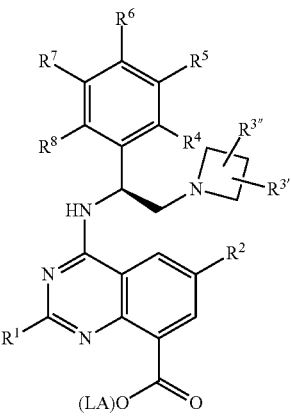

which is then converted to a carboxamide compound of Formula (II').

11. A method according to claim 6, wherein said compound has an Aurora B/p70S6K inhibitory ratio of at least 5.2.

12. A method according to claim 11, wherein said compound has an Aurora B/p70S6K inhibitory ratio of at least 15.2.

* * * * *

UNITED STATES PATENT AND TRADEMARK OFFICE
CERTIFICATE OF CORRECTION

PATENT NO. : 8,946,247 B2
APPLICATION NO. : 13/989199
DATED : February 3, 2015
INVENTOR(S) : Bayard R. Huck et al.

It is certified that error appears in the above-identified patent and that said Letters Patent is hereby corrected as shown below:

IN THE CLAIMS:

Column 51, lines 57-60 (Claim 3), read as follows:

-- 4-[(S)-2-Azetidin-1-yl-1-(4-isopropylphenyl)-ethy-lamino]-quinazoline-8-carboxylic acid amide;
   4-[(S)-2-Azetidin-1-yl-1-(4-isopropylphenyl)-ethy-lamino]-quinazoline-8-carboxylic acid
      amide; --

Should read as:

-- 4-[(S)-2-Azetidin-1-yl-l-(4-isopropylphenyl)-ethy-lamino]-quinazoline-8-carboxylic acid amide;
   4-[(S)-2-Azetidin-1-yl-1-(4-carbamoylphenyl)-ethy-lamino]-quinazoline-8-carboxylic acid amide;
   4-[(S)-2-Azetidin-1-yl-1-(4-isopropoxyphenyl)-ethy-lamino]-quinazoline-8-carboxylic acid
      amide; --

Column 53, lines 2-13 (Claim 10), the compound of Formula (V) presents as:

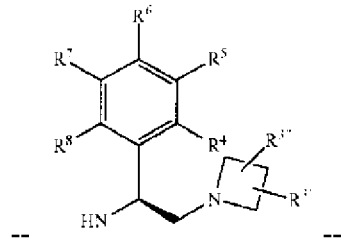

Should present as:

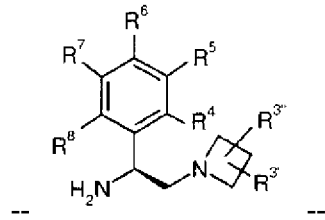

Signed and Sealed this
Eighteenth Day of August, 2015

Michelle K. Lee
*Director of the United States Patent and Trademark Office*